(12) United States Patent
Fujita et al.

(10) Patent No.: US 9,020,705 B2
(45) Date of Patent: Apr. 28, 2015

(54) BIOLOGICAL SIGNAL MEASURING DEVICE AND BIOLOGICAL STATE ANALYZING SYSTEM

(75) Inventors: Etsunori Fujita, Hiroshima (JP); Yumi Ogura, Hiroshima (JP); Shinichiro Maeda, Hiroshima (JP); Shigeyuki Kojima, Hiroshima (JP)

(73) Assignee: Delta Tooling Co., Ltd., Hiroshima-shi (JP)

( * ) Notice: Subject to any disclaimer, the term of this patent is extended or adjusted under 35 U.S.C. 154(b) by 1093 days.

(21) Appl. No.: 13/059,904

(22) PCT Filed: Jul. 28, 2009

(86) PCT No.: PCT/JP2009/063392
§ 371 (c)(1),
(2), (4) Date: Jun. 8, 2011

(87) PCT Pub. No.: WO2010/021229
PCT Pub. Date: Feb. 25, 2010

(65) Prior Publication Data
US 2011/0251522 A1    Oct. 13, 2011

(30) Foreign Application Priority Data

Aug. 19, 2008  (JP) ................. 2008-211212
Aug. 19, 2008  (JP) ................. 2008-211242
Sep. 1, 2008   (JP) ................. 2008-224179

(51) Int. Cl.
A61B 5/02     (2006.01)
A61B 5/024    (2006.01)
(Continued)

(52) U.S. Cl.
CPC ............... *A61B 5/024* (2013.01); *G08B 21/06* (2013.01); *A47C 9/002* (2013.01); *A61B 5/6887* (2013.01); *A61B 5/7239* (2013.01)

(58) Field of Classification Search
CPC ................................. A61B 5/024; G08B 21/06
USPC ......... 701/45, 46, 47; 702/138, 140; 340/575, 340/576; 280/735
See application file for complete search history.

(56) References Cited

U.S. PATENT DOCUMENTS 5,918,696 A * 7/1999 VanVoorhies .................. 180/273
5,987,370 A * 11/1999 Murphy et al. .................. 701/45
(Continued)

FOREIGN PATENT DOCUMENTS

JP    2002 187450    7/2002
JP    2007 90032     4/2007
(Continued)

OTHER PUBLICATIONS

U.S. Appl. No. 13/266,188, filed Oct. 25, 2011, Fujita, et al.
(Continued)

*Primary Examiner* — Thomas G Black
*Assistant Examiner* — Peter D Nolan
(74) *Attorney, Agent, or Firm* — Oblon, McClelland, Maier & Neustadt, L.L.P.

(57) ABSTRACT

A configuration is adopted where elastic members made of expanded rein beads and having a size covering air cushions are disposed between a skin member and the air cushions of a human body supporting device. By arranging a plurality of elastic members made of expanded rein beads and in a stacking manner, preferably, arranging two elastic members made of expanded resin beads, spring constants of the elastic members obtained from load-deflection characteristics when they are pressed to a deflection amount of 1 mm by a pressing plate with a diameter of 30 mm being higher than that of the air cushion and being different from each other, a biological signal can be transmitted to the air cushions without damping the biological signal, though the elastic members made of expanded rein beads and are provided.

17 Claims, 25 Drawing Sheets

(51) Int. Cl.
*G08B 21/06* (2006.01)
*A47C 9/00* (2006.01)
*A61B 5/00* (2006.01)

(56) References Cited

U.S. PATENT DOCUMENTS

| | | | |
|---|---|---|---|
| 6,043,736 A * | 3/2000 | Sawahata et al. | 340/438 |
| 6,056,079 A * | 5/2000 | Cech et al. | 180/273 |
| 6,058,341 A * | 5/2000 | Myers et al. | 701/45 |
| 6,088,642 A * | 7/2000 | Finkelstein et al. | 701/49 |
| 6,098,000 A * | 8/2000 | Long et al. | 701/49 |
| 6,101,436 A * | 8/2000 | Fortune et al. | 701/45 |
| 6,392,550 B1 * | 5/2002 | Najor | 340/576 |
| 6,490,936 B1 * | 12/2002 | Fortune et al. | 73/862.581 |
| 6,674,024 B2 * | 1/2004 | Cech et al. | 177/144 |
| 6,927,678 B2 * | 8/2005 | Fultz et al. | 340/438 |
| 6,966,577 B2 * | 11/2005 | Baba et al. | 280/735 |
| 7,000,948 B2 * | 2/2006 | Little et al. | 280/743.1 |
| 7,015,818 B2 * | 3/2006 | Takashima | 340/576 |
| 7,188,536 B2 * | 3/2007 | Waidner et al. | 73/862.454 |
| 7,219,923 B2 * | 5/2007 | Fujita et al. | 280/735 |
| 7,237,443 B2 * | 7/2007 | Speckhart et al. | 73/862.046 |
| 7,255,394 B2 * | 8/2007 | Ogura | 297/284.4 |
| 7,317,392 B2 * | 1/2008 | DuRocher | 340/562 |
| 7,470,231 B2 * | 12/2008 | Fujita et al. | 600/300 |
| 7,532,964 B2 * | 5/2009 | Fujita et al. | 701/36 |
| 7,609,168 B2 * | 10/2009 | Boverie | 340/576 |
| 8,151,654 B2 * | 4/2012 | Speckhart et al. | 73/862.454 |
| 2004/0032117 A1 * | 2/2004 | Pinto et al. | 280/735 |
| 2004/0061615 A1 | 4/2004 | Takashima | |
| 2006/0283652 A1 * | 12/2006 | Yanai et al. | 180/272 |
| 2010/0117411 A1 | 5/2010 | Fujita et al. | |
| 2010/0137725 A1 | 6/2010 | Takahashi et al. | |

FOREIGN PATENT DOCUMENTS

| | | |
|---|---|---|
| WO | 2007 055152 | 5/2007 |
| WO | 2008 044491 | 4/2008 |
| WO | 2008 099537 | 8/2008 |

OTHER PUBLICATIONS

U.S. Appl. No. 13/321,367, filed Nov. 18, 2011, Fujita, et al.
International Search Report issued Aug. 25, 2009 in PCT/JP09/63392 filed Jul. 28, 2009.
U.S. Appl. No. 13/059,904, filed Feb. 18, 2011, Fujita, et al.

* cited by examiner (a)

(b)

BIOLOGICAL SIGNAL MEASURING DEVICE AND BIOLOGICAL STATE ANALYZING SYSTEM

TECHNICAL FIELD

The present invention relates to a technique of detecting a biological signal to analyze a biological state, and in particular to a biological signal measuring device and a biological state analyzing system where an air cushion which can detect a biological signal non-invasively is used.

BACKGROUND ART

In recent years, monitoring a biological state of a driver during vehicle driving has drawn attention as an accident prevention measure. The present applicant also discloses a system which is provided with an airbag having a three-dimensional solid knitted fabric inserted therein, where the airbag is disposed at a site corresponding to, for example, a human lumbar area, an air pressure fluctuation of the airbag is measured and human's biological signals are detected from time-series data of the air pressure fluctuation obtained, so that a human's biological state is analyzed. In Non-Patent Literatures 1 and 2, further, trials where an air pack sensor is disposed along a lumbar iliocostal muscle to detect a human's biological signal have been reported.

CITATION LIST

Patent Literature 1: Japanese Patent Application Laid-Open No. 2007-90032
Non-Patent Literature 1: "APPLICATION OF BIOLOGICAL WANDERING SIGNAL MEASURED BY NON-INVASIVE TYPE SENSOR TO FATIGUE AND SLEEP ONSET PREDICTION" by Naoki OCHIAI (other 6 persons), 39-th Japan Ergonomics Society; Chugoku and Shikoku Branch Convention, Collection of Lectures and Papers issued on Nov. 25, 2006 from Japan Ergonomics Society; Chugoku and Shikoku Branch Secretariat
Non-Patent Literature 2: "TRIAL PRODUCTION OF VEHICLE SEAT HAVING NON-INVASIVE BIOLOGICAL SIGNAL SENSING FUNCTION" by Shinichiro MAEDA (other 4 persons), 39-th Japan Ergonomics Society Chugoku and Shikoku Branch Convention, Collection of Lectures and Papers issued on Nov. 25, 2006 from Japan Ergonomics Society Chugoku and Shikoku Branch Secretariat

SUMMARY OF INVENTION

Technical Problem

The patent literature 1 and non-patent literatures 1 and 2 show that it is possible to detect pulse waves from the vicinity of a lumbar area of a person to utilize them for analysis of a biological state of the person, but, since air pack sensors (air cushions) shown in these literatures are vertically long and are disposed on both side portions of a seatback section, when a person sits on this seat, he/she feels the air cushions as foreign objects easily. Though a cushion material for reducing the foreign object feeling is disposed between the air cushions and a human body in order to solve such a problem, when such a cushion material is disposed, detection sensitivity of biological signals detected by the air cushion becomes dull. Further, when a person sits on a seat for such a vehicle as an automobile, vibrations transmitted from a seatback section act as noises, so that an idea for removing the noises is required. Though various ideas for removing the noises have also been proposed in the above-described conventional arts, as well as the ideas, it is further desirable that influence of external vibrations can be reduced as much as possible.

The present invention has been made in view of the above, and an object thereof is to provide a biological signal measuring device where, while a person sitting on human body supporting means such as a vehicle seat is prevented from feeling a foreign object, a biological signal can be detected with a high sensitivity, and a removal effect of vibrations inputted externally is high, and a biological signal analyzing system using the biological signal measuring device.

Solution of Problem

In order to solve the above problem, a biological signal measuring device of the present invention comprises an air cushion provided with an airbag and a sensor which detects air pressure fluctuation of the airbag according to load fluctuation, where the air cushion is assembled between a skin member and a cushion supporting member arranged on a back face side of the skin member at a site supporting at least the vicinity of a lumber area of a person in human body supporting means, and an output signal of the sensor is transmitted to state analyzing means which analyzes a state of the person, wherein
an elastic member made of expanded resin beads which has a size covering the air cushion is disposed between the skin member and the air cushion.

It is preferred that the elastic member made of expanded resin beads is configured by stacking a first elastic member made of expanded resin beads and a second elastic member made of expanded resin beads to each other, and each of the first elastic member made of expanded resin beads and the second elastic member made of expanded resin beads comprises an expanded bead body and a covering material covering an outer face of the expanded bead body.

It is preferred that the covering material covering the expanded bead body configuring one of the first elastic member made of expanded resin beads and the second elastic member made of expanded resin beads is different in retractility from the covering material covering the expanded bead body configuring the other.

It is preferred that the covering material covering the expanded bead body configuring one of the first elastic member made of expanded resin beads and the second elastic member made of expanded resin beads is an elastic fiber nonwoven fabric formed by melting and bonding thermoplastic elastomer elastic fibers mutually, and the covering material covering the expanded bead body configuring the other is a nonwoven fabric made of thermoplastic polyester small in retractility than the elastic fiber nonwoven fabric.

Further, it is preferred that polyester films are stuck to a surface of the first elastic member made of expanded resin beads and a back face of the second elastic member made of expanded resin beads, respectively.

It is preferred that both spring constants of the first and second elastic members made of expanded resin beads obtained by load-deflection characteristics when the first and second elastic members made of expanded resin beads are disposed on the air cushion placed on a measuring stand, respectively, and the first and second elastic members made of expanded resin beads are pressed to a deflection amount of 1 mm by using a pressing plate with a diameter of 30 mm are higher than a spring constant of the air cushion obtained from a load-deflection characteristic when only the air cushion is pressed to a deflection amount of 1 mm by using a pressing plate with a diameter of 30 mm, the spring constant of one of the first and second elastic members made of expanded resin beads falls within a range of 1.1 to 1.4 times the spring constant of the other, and a spring constant obtained from a load-deflection characteristic when the first and second elastic members made of expanded resin beads are stacked to each other to be disposed on the air cushion placed on a measuring stand and the first and second elastic members made of expanded resin beads are pressed to a deflection amount of 1 mm by using a pressing plate with a diameter of 30 mm falls within a range of 0.8 to 1.2 times the spring constant of only the air cushion.

It is preferred that a three-dimensional solid knitted fabric is disposed within an airbag of the air cushion.

It is preferred that the air cushion comprises a plurality of small airbags having a predetermined length and connected to one another in their length directions, where air is prevented from flowing between adjacent ones of the small airbags, and three-dimensional solid knitted fabrics disposed in the respective small airbags, and air pressure fluctuation of any of the small airbags is measured.

It is preferred that the air cushion has a predetermined length and is configured such that at least two air cushions are stacked for use, a surface side air cushion of the at least two air cushions which is disposed on the side of the skin member of the human body supporting means comprises a plurality of small airbags connected to one another in their length directions, where air is prevented from flowing between adjacent ones of the small airbags, and three-dimensional solid knitted fabrics disposed in the respective small airbags, and air pressure fluctuation of any of the small airbags is measured.

It is preferred that the small airbag which measures the air pressure fluctuation is a small airbag of the plurality of small airbags which is positioned in an area where pulse waves of an aorta of a dorsal region of the person can be detected.

It is preferred that the human body supporting means is a seat provided with a seat cushion section and a seatback section, the air cushion is disposed along a vertical direction of the seatback section, and the small airbag which measures the air pressure fluctuation has a width of 40 to 100 mm and a length of 120 to 200 mm and is provided such that an intersecting portion of one of side edges thereof positioned nearer to the center of the seatback section and a lower edge thereof is set to fall in a length range of 150 to 280 mm from an upper face of the seat cushion section along a surface of the seatback section and fall in a range of 60 to 120 mm from the center of the seatback section.

It is preferred that the air cushion is configured such that two air cushions are provided at bilaterally symmetric positions regarding the center of the seatback section, and air pressure fluctuation of a small airbag in one of the two air cushions is measured.

It is preferred that the respective air cushions have a width of 40 to 100 mm and an entire length of 400 to 600 mm, and the respective air cushions are received in cushion receiving portions of a receiving body provided with a connection portion with a width of 60 to 120 mm and the cushion receiving portions provided on both sides of the connection portion, resulting in unitization.

It is preferred that widths of the first and second elastic members made of expanded resin beads are equal to or longer than a length between top portions of the two air cushions.

A biological state analyzing system of the present invention comprises the biological signal measuring device; and state analyzing means for analyzing a state of a person supported by the human body supporting means from an output signal of the sensor which detects air pressure fluctuation of the air cushion in the biological signal measuring device.

It is preferred that the state analyzing means comprises: power value slope calculating means which calculates a difference between an upper limit side peak value and a lower limit side peak value for each predetermined time range from peak values of each cycle of a time series waveform of an output signal obtained by the sensor in the biological signal measuring device, and utilizes the difference as a power value to obtain time series data of the power value and performs slide calculation by a predetermined number of times to obtain a slope of the power value to a time axis in the predetermined time range;

maximum Liapunov index slope calculating means which obtains time series data of a maximum Liapunov index from the time series waveform of the output signal obtained by the sensor in the biological signal measuring device and performs slide calculation by a predetermined number of times to obtain a slope of the maximum Liapunov index to the time axis in the predetermined time range; and sleep onset prediction determining means which, when respective two slope time series waveforms obtained from the power value slope calculating means and the maximum Liapunov index slope calculating means are superimposed on each other, determines portions of the two slope time series waveforms which have opposite phases to each other as a sleep onset prediction signal.

It is preferred that the state analyzing means further has differentiated waveform calculating means which differentiates the time series waveform of the output signal obtained from the sensor in the biological signal measuring device to obtain a differentiated waveform, and the power value slope calculating means and the maximum Liapunov index slope calculating means calculate a power value slope and a maximum Liapunov index slope from the differentiated waveform obtained from the differentiated waveform calculating means.

It is preferred that the state analyzing means further has slope time series differentiated waveform calculating means which differentiates a time series waveform of the power value slope obtained by the power value slope calculating means and a time series waveform of the maximum Liapunov index slope obtained by the maximum Liapunov index slope calculating means to obtain differentiated waveforms of the respective slope time series waveforms.

Advantageous Effects of Invention

In the present invention, the configuration where the elastic member made of expanded resin beads which has a size covering the air cushion is disposed between the skin member of the human body supporting means and the air cushion is adopted. By providing the elastic member made of expanded resin beads, a foreign object feeling due to provision of the air cushion is eliminated. By arranging a plurality of the elastic members made of expanded resin beads in a stacking manner, preferably, disposing two elastic members made of expanded resin beads, spring constants thereof obtained from load-deflection characteristics when the elastic members made of expanded resin beads are pressed to a deflection amount of 1 mm by a pressing plate with a diameter of 30 mm, respectively, being higher than the spring constant of the air cushion and being different from each other, a biological signal can be transmitted to the air cushion without decaying. Accordingly, when the elastic member made of expanded resin beads is disposed, while a foreign object feeling is reduced, measurement of a biological signal can be detected with sensitivity similar to that in the case where the elastic member made of expanded resin beads is not disposed.

DESCRIPTION OF EMBODIMENTS

Figure 1:
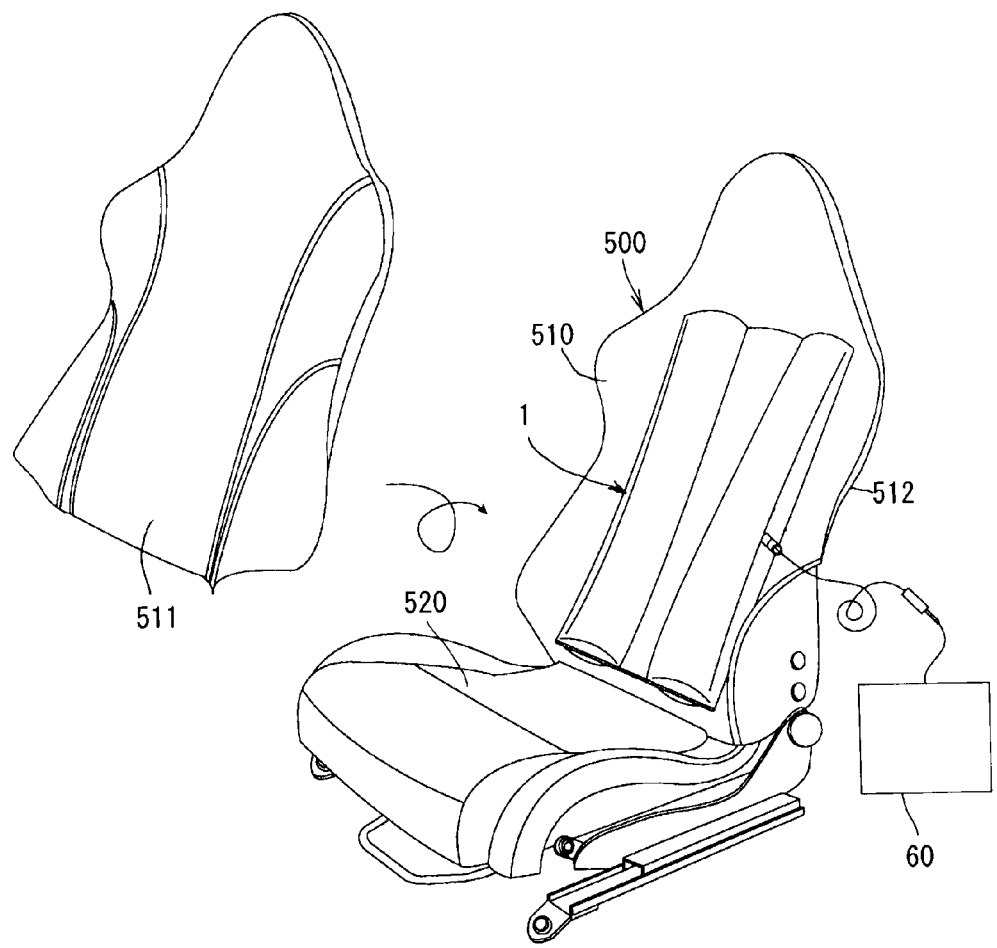
FIG. 1 is a diagram showing a state where a biological signal measuring device according to an embodiment of the present invention has been assembled into a seat.

Hereinafter, embodiments of the present invention will be further explained in detail with reference to the drawings. FIG. 1 is a diagram showing an appearance of a seat 500 for an automobile assembled with a biological signal measuring device 1 according to this embodiment. As shown in this figure, the biological signal measuring device 1 is assembled into a seatback section 510 for use.

Figure 3:
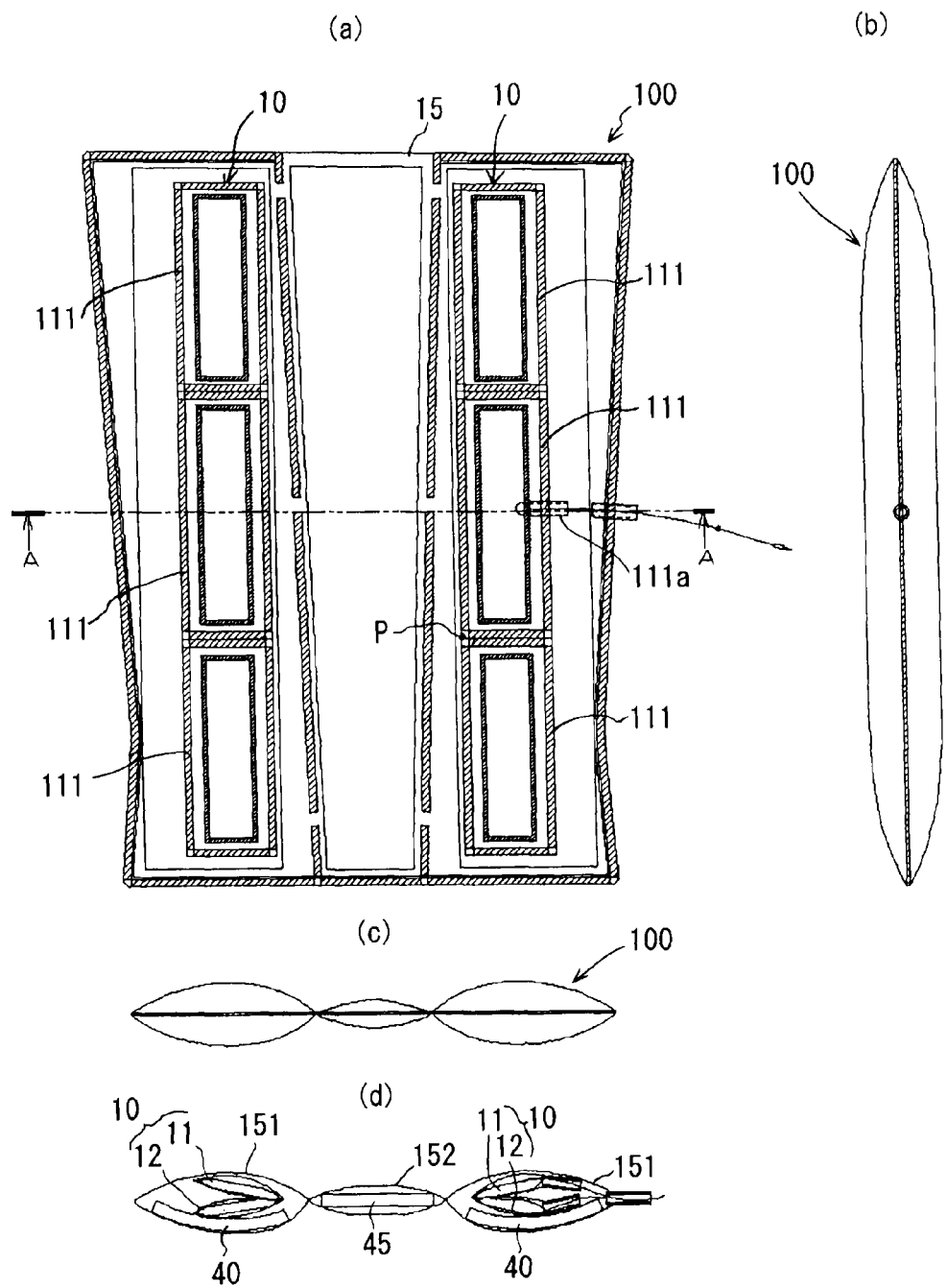
FIGS. 3A to 3D are diagrams showing an air cushion unit, FIG. 3A being a sectional view of the air cushion unit viewed from a front face thereof, FIG. 3B being a side view of the air cushion unit, FIG. 3C being a bottom view of the air cushion unit, and FIG. 3D being a sectional view of the air cushion unit taken along line A-A in FIG. 3A.
Figure 4:
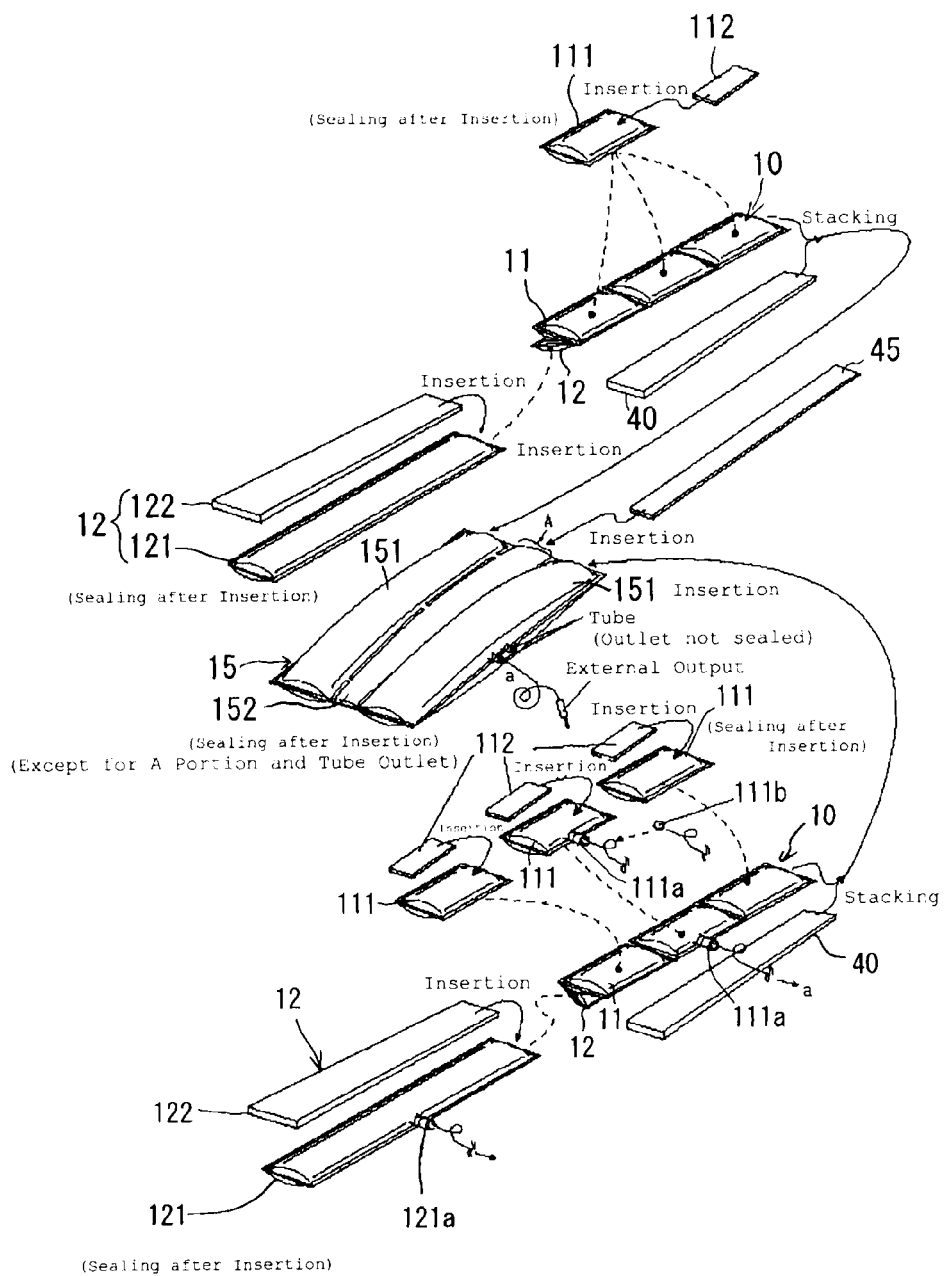
FIG. 4 is an exploded perspective view of the air cushion unit.

The biological signal measuring device 1 comprises an air cushion unit 100, a first elastic member made of expanded resin beads 20, and a second elastic member made of expanded resin beads 30. The air cushion unit 100 comprises one receiving body 15 and two air cushions 10 received in the receiving body 15. As shown in FIG. 3 and FIG. 4, the air cushions 10 each comprise a surface side air cushion 11 and a back side air cushion 12 stacked on each other, and they are arranged on left side and right side portions of the receiving body 15. The surface side air cushion 11 has a configuration where three small airbags 111 are connected vertically in series, while the respective small airbags 111 are formed so as to prevent air from flowing from one to another, respectively. Three-dimensional solid knitted fabrics 112 are disposed in the respective small airbags 111 as resilience imparting members.

The back side air cushion 12 comprises a large airbag 121 with the same length as the entire length of the surface side air cushion 11 comprising three small airbags 111 connected in series, and a three-dimensional solid knitted fabric 122 received in the large airbag 121 as a resilience imparting member (see FIG. 4). The surface side air cushion 11 and the back side air cushion 12 are used, after they are joined to each other at their one edges extending along their longitudinal directions and they are folded about the joined edges to be stacked on each other (see FIG. 3D and FIG. 4).

In this embodiment, the air cushions 10 obtained by stacking the surface side air cushion 11 and the back side air cushion 12 mutually in this manner are arranged on the left side and the right side. The arrangement of the respective air cushions 10 on the left side and the right side makes contact of the seatback section to the back of a seat-sitting person bilaterally even, so that his/her uncomfortable feeling is reduced. Further, a sensor-mounting tube 111a is provided to one of the small airbags 111 configuring one of the left and right surface side air cushions 11 and 11, and a sensor 111b which measures air pressure fluctuation is fixed inside the small airbag 111. Incidentally, the sensor-mounting tube 111a is sealed. Though the sensor may be disposed in the large airbag 121 configuring the back side air cushion 12, if the sensor is provided in an airbag having a large volume, there is a possibility that air pressure fluctuation due to pulse waves is absorbed by the airbag, so that it is preferred that the sensor is provided in the small airbag 111. As shown in FIG. 4, however, such a configuration can be adopted that the sensor is preliminarily arranged in the site where a mounting tube 121a has been provided in the large airbag 121, so that a result obtained by measuring air pressure fluctuation in the large airbag 121 is utilized for verification of the measurement result of the small airbag 111 as necessary. In order to cause the small airbag 111 to respond to air pressure fluctuation due to such a biological signal rapidly, it is preferred that the size of the small airbag 111 has a width in the range of 40 to 100 mm and a length in the range of 120 to 200 mm. A material for the small air bag 111 is not limited to specific ones, but it can be formed of a sheet made of, for example, polyurethane elastomer (for example, Product Number "DUS605-CDR" produced by Sheedom Co., Ltd.). As the sensor 111b, one which can measure air pressure in the small airbag 111 can be used, for example, a capacitive microphone sensor can be used.

As the size of the large airbag 121 and the entire size of the three small airbags 111 connected in series, it is preferred that, when these airbags are used in the seatback section 510 of the seat 500 for an automobile, the sizes are set such that their widths and their entire lengths are in a range of 40 to 100 m and a range of 400 to 600 mm, respectively. When the length is short, a seat-sitting person feels uncomfortable at only a portion of the seat positioned near his/her lumbar area in the seatback section 510, so that it is preferred that the length is set to 400 mm or more and the airbags are caused to accommodate the entire back of the seat-sitting person as much as possible.

Incidentally, in the embodiment, the air cushion 10 is configured by stacking the surface side air cushion 11 and the back side air cushion 12 mutually, but it may be composed of only the surface side air cushion 11.

In the embodiment, the sensor 111b detecting air pressure fluctuation is provided in the small airbag 111 of the small airbags ill which is positioned at the center of the surface side air cushion 11 configuring the air cushion 10 arranged on the left side of the seat-sitting person. The position of the small airbag 111 corresponds to a region where pulse waves of an aorta (especially, a downward aorta) of the dorsal region of the seat-sitting person are detectable. Though regions where pulse waves of an aorta of the dorsal region are detectable are not uniform due to the frames of seat-sitting persons, as the result of measurement of 20 subjects having various frames from a 158-centimeter-tall Japanese woman to a 185-centimeter-tall Japanese man, pulse waves of the aortas of all the subjects could be detected when an intersecting portion P (see FIG. 2 and FIG. 3) of a side edge of the small airbag 111 (having a width of 60 mm and a length of 160 mm) positioned nearer to the center of the seatback section 510 and a lower edge thereof was set such that a length L from an upper face of the seat cushion section 520 along a surface of the seatback section 510 was 220 mm and a distance M from the center of the seatback section 510 was 80 mm. When the size of the small airbag 111 is set such that its width is in a range of 40 to 100 mm and its length is in a range of 120 to 200 mm, it is preferred that the position of the intersecting portion P is set such that the length from the upper face of the seat cushion section 520 along the surface of the seatback section 510 is in a range of 150 to 280 mm and the distance from the center of the seatback section 510 is in a range of 60 to 120 mm.

Figure 2:
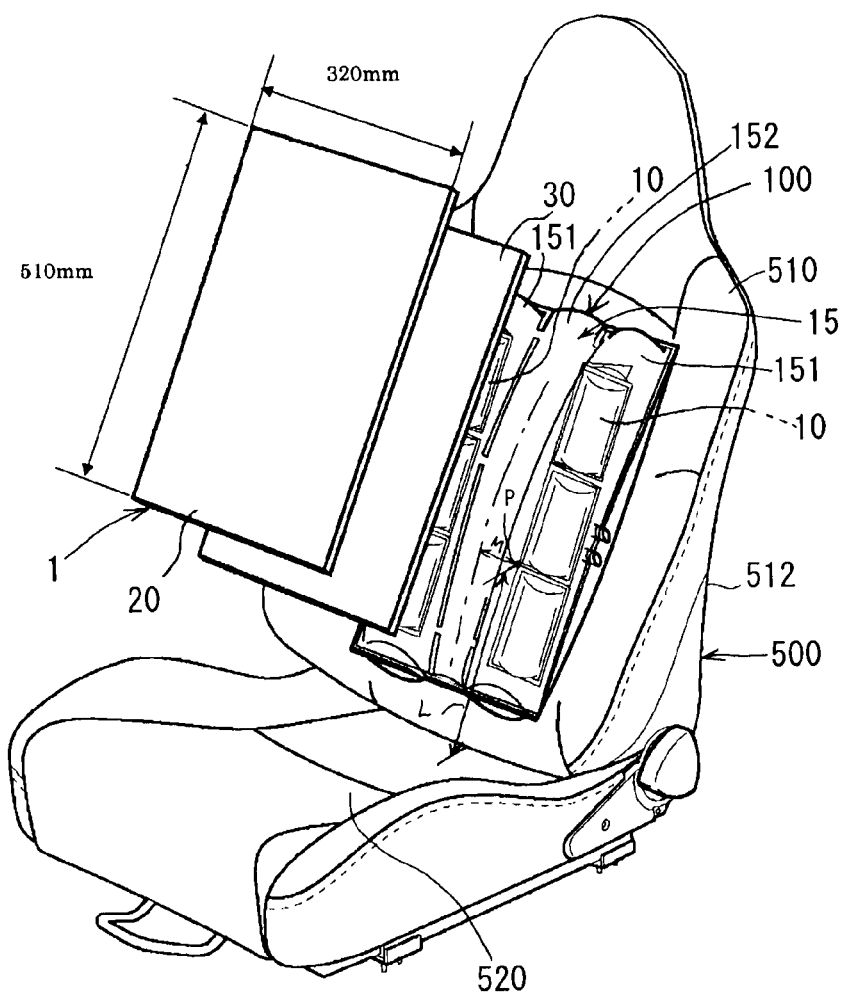
FIG. 2 is a diagram showing the biological signal measuring device according to the above embodiment in detail.

It is preferred that the above two air cushions 10 are unitized such that they can be easily set at predetermined positions in the seatback section 510. Therefore, it is preferred that an air cushion unit 100 obtained by loading the air cushions 10 into the receiving body 15 such as shown in FIG. 2 to FIG. 4 is configured. The receiving body 15 has bag-shaped air cushion receiving portions 151 receiving the air cushion 10 on both sides, and it has a connecting portion 152 connecting between two air cushion receiving portions 151.

The air cushions 10 are inserted into two air cushion receiving portions 151, respectively. It is also preferred that a three-dimensional solid knitted fabric 40 with approximately the same size as the air cushion 10 is inserted into the air cushion receiving portion 151 so as to be positioned on a back face side of the back side air cushion 12 of the air cushion 10 in a stacking manner (see FIG. 3D). By arranging the three-dimensional solid knitted fabric 40, an effect of removing vibrations inputted into a human body via the seatback section 510 is further improved.

The connecting portion 152 may be a member which can support two air cushion portions 151 spaced from each other by a predetermined distance, and it is formed to have a width of about 60 to 120 mm. It is preferred that the connecting portion 152 is formed in a bag shape, so that a three-dimensional solid knitted fabric 45 is inserted into the connecting portion 152 (see FIG. 3D and FIG. 4). Thereby, vibrations inputted via the connecting portion 152 can also be removed effectively by inserting the three-dimensional solid knitted fabric 45 into the connecting portion 152.

Incidentally, as described above, the small airbag 111 can be formed of a sheet made of, for example, polyurethane elastomer (for example, Product Number "DUS605-CDR" produced by Sheedom Co., Ltd.), but it is preferred that the large airbag 121 configuring the back side cushion member 12 and the receiving body 15 are also made of the same material as that for the small airbag 111. The respective three-dimensional solid knitted fabrics loaded into the small airbags 111, the large airbag 121, the air cushion receiving portion 151, and the connecting portion 152 are knitted fabrics having a solid three-dimensional structure having a pair of ground knitted fabrics disposed separately from each other and a lot of connecting strands reciprocated between the pair of ground knitted fabrics to connect both the ground knitted fabrics, for example, as disclosed in JP-A-2002-331603.

One of the ground knitted fabrics is formed, for example, in a flat knitted fabric texture (fine mesh) continuing both in a wale direction and in a course direction from yarns obtained by twisting a monofilament, and the other ground knitted fabric is formed, for example, in a knitted stitch structure having a honeycomb-shaped (hexagonal) mesh from yarns obtained by twisting short fibers. Of course, the knitted fabric texture is arbitrary, any knitted fabric texture other than the fine mesh texture and the honeycomb shape can be adopted, the fine mesh texture can be adopted for both the ground knitted fabrics, and a combination of the knitted fabric textures can be set arbitrarily. The connecting strands are knitted between the two ground knitted fabrics such that one of the ground knitted fabrics and the other thereof are kept away from each other by a predetermined distance. As such a three-dimensional solid knitted fabric, for example, materials described below can be used. Incidentally, the respective three-dimensional solid knitted fabrics can be used in a state that a plurality of the three-dimensional solid knitted fabrics has been stacked one on another as necessary.

(1) Product Number: 49076D (produced by Suminoe Textile Co., Ltd.)

Material:

Surface side ground knitted fabric ••• twisted yarn of polyethylene terephthalate fiber false-twisted textured yarn of 300 decitex/288f and polyethylene terephthalate fiber false-twisted textured yarn of 700 decitex/192f Back side ground knitted fabric ••• combination of polyethylene terephthalate fiber false-twisted textured yarn of 450 decitex/108f and poly-trimethylene terephthalate monofilament of 350 decitex/1f Connecting strand ••••••• poly-trimethylene terephthalate monofilament of 350 decitex/1f (2) Product Number: 49013D (produced by Suminoe Textile Co., Ltd.)

Material:

Surface side ground knitted fabric ••• twisted yarn of two polyethylene terephthalate fiber false-twisted textured yarns of 450 decitex/108f Back side ground knitted fabric ••• twisted yarn of two polyethylene terephthalate fiber false-twisted textured yarns of 450 decitex/108f Connecting strand ••••••• poly-trimethylene terephthalate monofilament of 350 decitex/1f (3) Product Number: 69030D (produced by Suminoe Textile Co., Ltd.)

Material:

Surface side ground knitted fabric ••• twisted yarn of two polyethylene terephthalate fiber false-twisted textured yarns of 450 decitex/144f Back side ground knitted fabric ••• combination of polyethylene terephthalate fiber false-twisted textured yarn of 450 decitex/144f and poly-trimethylene terephthalate monofilament of 350 decitex/1f Connecting strand ••••••• poly-trimethylene terephthalate monofilament of 350 decitex/1f (4) Product Number produced by Asahi Kasei Fibers Corporation: T24053AY5-1S The first elastic member made of expanded resin beads 20 and the second elastic member made of expanded resin beads 30 are disposed between a skin member of the seatback section 510 and the receiving body 15 (the air cushion unit 100) which has received the air cushions 10 therein, they have a length corresponding to the entire length of two air cushions 10, and they have a width corresponding to a length between top portions of two air cushions 10. Therefore, it is preferred that members having such a size that a length is in a range of 400 to 600 mm and a width is in a range of about 250 to 350 mm are used. Thereby, since two air cushions 10 are covered with these members, undulation feeling due to the two air cushions 10 is reduced.

The first elastic member made of expanded resin beads 20 is composed of an expanded bead body formed in a flat plate shape and a covering material caused to adhere to an outer face of the expanded bead body. As the expanded bead body, an expanded formation body made by a bead method of resin containing at least one of polystyrene, polypropylene, and polyethylene is used. Incidentally, an expansion ratio is set arbitrarily and it is not limited to specific ones. The covering material is caused to adhere to an outer face of the expanded bead body by adhesive, and it is a material having a high extension percentage and a high recovery rate, so that an elastic fiber nonwoven fabric whose extension percentage is at least 200% and whose recovery rate at 100% extension percentage time is 80% is preferably used. For example, a nonwoven fabric where thermoplastic elastomer elastic fibers have been stuck to one another in a melting manner, which is disclosed in JP-A-2007-92217, can be used. Specifically, trade name "Espansione" produced by KB SEIREN, LTD. can be used.

The second elastic member made of expanded resin beads 30 is configured to have an expanded bead body like the first elastic member made of expanded reins beads 20, but as a covering material for covering an outer face of the expanded bead body, a material with a retractility smaller than that of the elastic fiber nonwoven fabric used in the first elastic member made of expanded resin beads 20, for example, a nonwoven fabric made of thermoplastic polyester is used. Specifically, a biaxial fabric (longitudinal: 20/inch, horizontal: 20/inch) formed from polyethylene naphthalate (PEN) fibers (1100 dtex) produced by TEIJIN LIMITED can be used.

The order of stacking the first elastic member made of expanded resin beads 20 and the second elastic member made of expanded resin beads 30 is not limited, but it is preferred that the first elastic member made of expanded resin beads 20 having a higher elasticity is disposed on a side nearer the skin member 511 of the seatback section 510. The expanded bead body configuring the first and second elastic members made of expanded resin beads 20 and 30 is set to have a thickness of about 5 to 6 mm, and formation thereof is achieved by causing a nonwoven fabric made of the above-described elastic fiber nonwoven fabric or thermoplastic polyester having a thickness of about 1 mm to adhere to an outer face thereof. Incidentally, in the embodiment, polyester films such as a PEN film are stuck to a face of the first elastic member made of expanded resin beads 20 opposed to the skin member 511 and a face of the second elastic member made of expanded resin beads 30 opposed to the air cushion unit 100, respectively. Thereby, transmissibility of a biological signal is improved.

In the embodiment, the seatback section 510 of the seat 500 configuring the human body supporting means is provided with the skin member 511 and a cushion supporting member 512 disposed on a back face side of the skin member 511, and the receiving body 15 holding the air cushions 10 (the air cushion unit 100) and the first and second elastic members made of expanded resin beads 20 and 30 are assembled between the skin member 511 and the cushion supporting member 512. At this time, the receiving body 15 holding the air cushions 10 (the air cushion unit 100) is first disposed on the side of the cushion supporting member 512, the second elastic member made of expanded resin beads 30 is disposed on a surface side of the receiving body 15, and after the first elastic member made of expanded resin beads 20 is further disposed on a surface side of the second elastic member made of expanded resin beads 30, these members are covered with the skin member 511. Incidentally, the cushion supporting member 512 can be formed by stretching a three-dimensional solid knitted fabric between rear end edges of a pair of left and right side frames of the seatback section 510 or can be formed of a synthetic resin plate. The skin member 511 can be provided by stretching, for example, a three-dimensional solid knitted fabric, an artificial leather, a leather, or a laminated body of these members between front edges of the pair of left and right side frames.

In this embodiment, thus, since the configuration where the first elastic member made of expanded resin beads 20 and the second elastic member made of expanded resin beads 30 which have a predetermined size are disposed on the back side of the skin member 511 in a stacking manner and the receiving body 15 holding a pair of left and right air cushions 10 (the air cushion unit 100) is further disposed behind them is adopted, a seat-sitting person is prevented from feeling undulation of the air cushions 10 on his/her back, and sitting feeling is improved though the configuration having the air cushions 10 for measuring a biological signal is adopted.

Test Example 1

Static Load Characteristic

Figure 5:
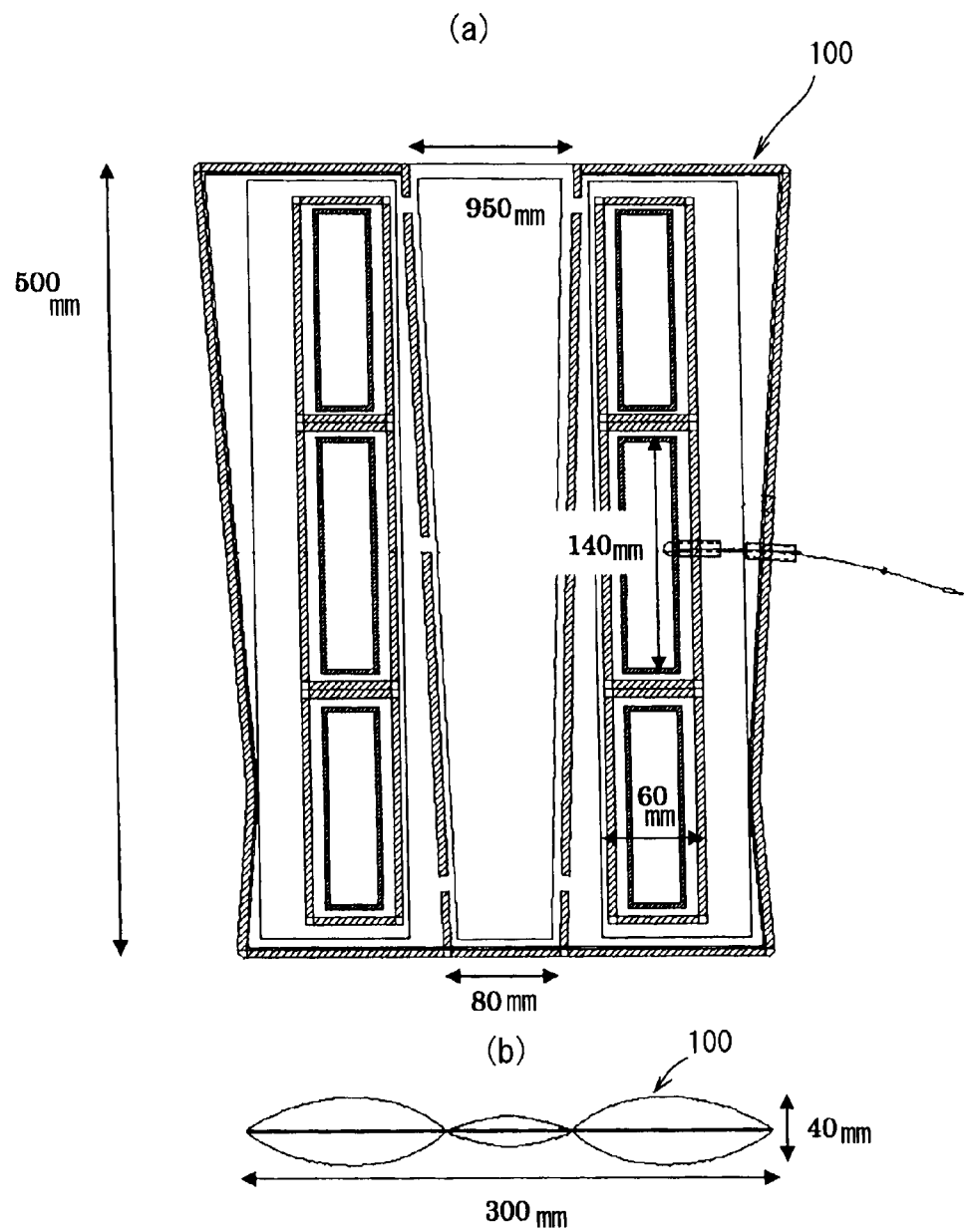
FIGS. 5A and 5B are diagrams for explaining sizes of an air cushion unit used in a test example.
Figure 6:
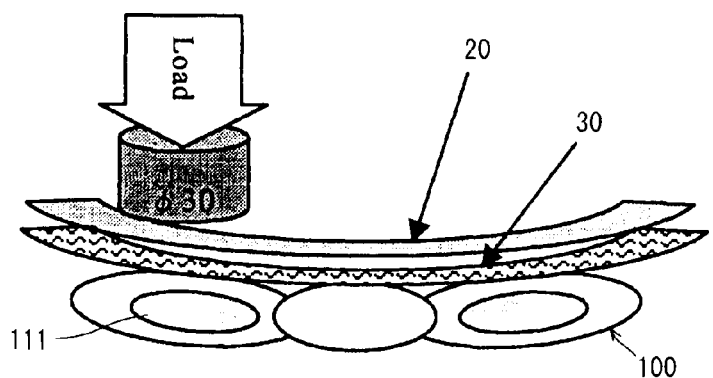
FIG. 6 is a diagram for explaining a measuring method of a load-deflection characteristic in Test Example 1.

As shown in FIG. 6, regarding a case where only the receiving body 15 holding the air cushions 10 (the air cushion unit 100) was placed on a measuring board alone (data of "air pack" in FIG. 7), a case where the first elastic member made of expanded resin beads 20 was stacked on the receiving body 15 holding the air cushions 10 (the air cushion unit 100) (data of "A+air pack" in FIG. 7), a case where the second elastic member made of expanded resin beads 30 was stacked on the receiving body 15 holding the air cushions 10 (the air cushion unit 100) (data of "B+air pack" in FIG. 7), and a case where the second elastic member made of expanded resin beads 30 was stacked on the receiving body 15 holding the air cushions 10 (the air cushion unit 100) and the first elastic member made of expanded resin beads 20 was further stacked thereon (data of "A+B+air pack" in FIG. 7), load-deflection characteristics were measured by pressing a position corresponding to the small airbag 111 additionally provided with the sensor 111b to a deflection amount of 1 mm by a pressing plate with a diameter of 30 mm. The three-dimensional solid knitted fabrics received in the respective airbags 111 and 121 of the air cushions 10 were materials having Product Number 49013D produced by Suminoe Textile Co., Ltd., and sizes of the respective sites were as shown in FIGS. 5A and 5B.

Figure 7:
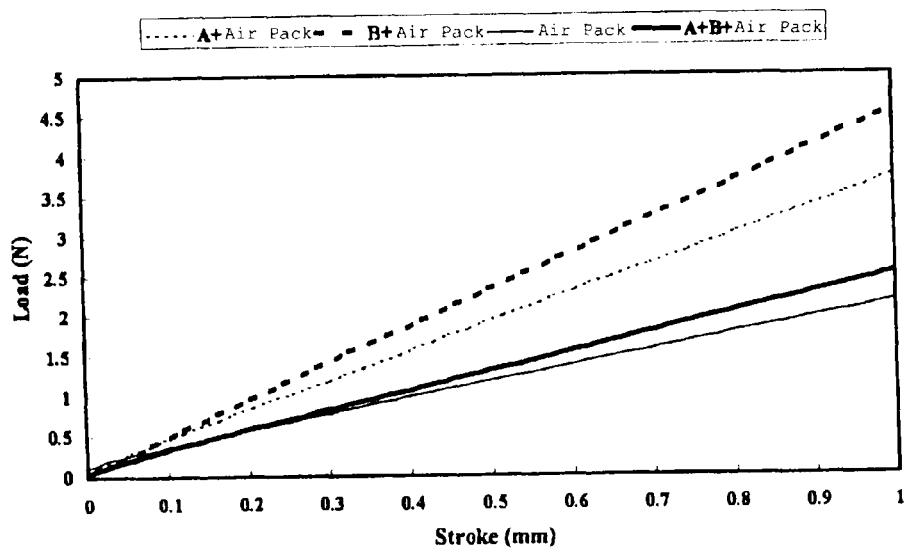
FIG. 7 is a graph showing a measurement result in FIG. 6.

The result is shown in FIG. 7. Air pressure fluctuation of the air cushions 10 held by the receiving body 15 caused by pulse waves of an aorta of a dorsal region of a person depends on the load-deflection characteristic obtained in the case where only the receiving body 15 holding the air cushions 10 was placed on a measuring board alone ("air pack" in FIG. 7). Therefore, when a spring constant becomes higher than the load-deflection characteristic, the sensitivity of pulse waves of an aorta becomes duller than that in the case where the receiving body 15 holding the air cushions 10 was directly disposed on the back face of the skin member 511. In view of this, when comparison of spring constants obtained from the respective load-deflection characteristics is performed, it is understood that the spring constant obtained in the case where both the first and second elastic members made of expanded resin beads 20 and 30 were stacked on the air cushion unit 100 (the receiving body 15 holding the air cushions 10) ("A+B+air pack" in FIG. 7) is closer to the spring constant obtained in the case where only the air cushion unit 100 (the receiving body 15 holding the air cushions 10) was placed on a measuring board alone and measurement was performed than the spring constant obtained in the case that only one of the first and second elastic members made of expanded resin beads 20 and 30 was stacked on the air cushion unit 100 (the receiving body 15 holding the air cushions 10) ("A+air pack" or "B+air pack" in FIG. 7). Accordingly, when both the first and second elastic members made of expanded resin beads 20 and 30 are used in a stacked manner thereof, although these members are stacked on the air cushions 10, transmission of pulse waves can be achieved with less attenuation of the pulse waves and foreign object feeling is reduced unlike the case where the air cushion 10 is used alone. Incidentally, when a plurality of the first elastic members made of expanded resin beads 20 were stacked on the air cushion unit 100 or when a plurality of the second elastic members made of expanded resin beads 30 were stacked on the air cushion unit 100, a result which was not so different from data of "A+air pack" or data "B+air pack" in FIG. 7 was obtained. Therefore, it is preferred that the first elastic member made of expanded resin beads 20 and the second elastic member made of expanded resin beads 30 are configured differently regarding their spring constants and they are stacked on the cushion unit 100. From the experimental result shown in FIG. 7, it is preferred that the spring constant of the second elastic member made of expanded resin beads 30 is set to 1.1 to 1.4 times the spring constant of the first elastic member made of expanded resin beads 20. As described above, this characteristic is provided by covering the first elastic member made of expanded resin beads 20 with an elastic fiber nonwoven fabric having a relatively high retractility and covering the second elastic member made of expanded resin beads 30 with a nonwoven fabric with a relatively low retractility. Further, it is preferred that the spring constant obtained in the case where the second elastic member made of expanded resin beads 30 is stacked on the receiving body 15 holding the air cushions 10 and the first elastic member made of expanded resin beads 20 is further stacked thereon ("A+B+air pack" in FIG. 7) is in a range of 0.8 to 1.2 times the spring constant shown by "air pack" in FIG. 7 corresponding to the spring constant of only the air cushions 10.

Test Example 2

Influence of Disturbance Vibration

Figure 8:
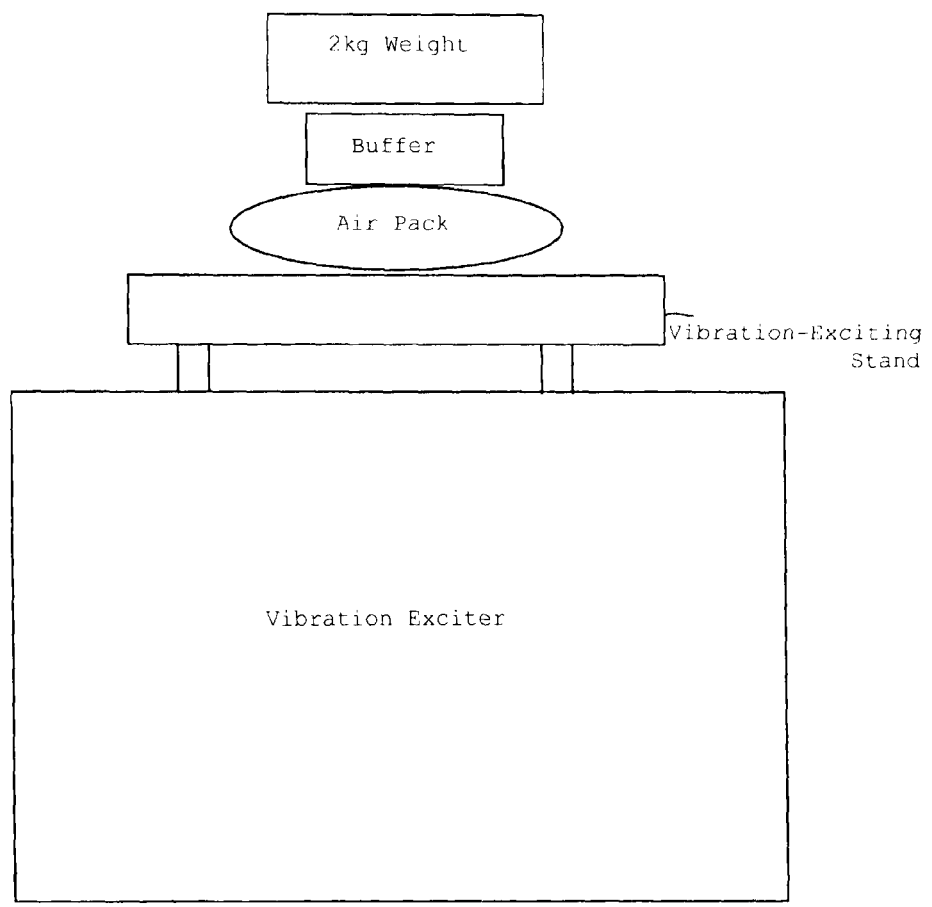
FIG. 8 is a diagram for explaining a test method for Test Example 2.
Figure 9:
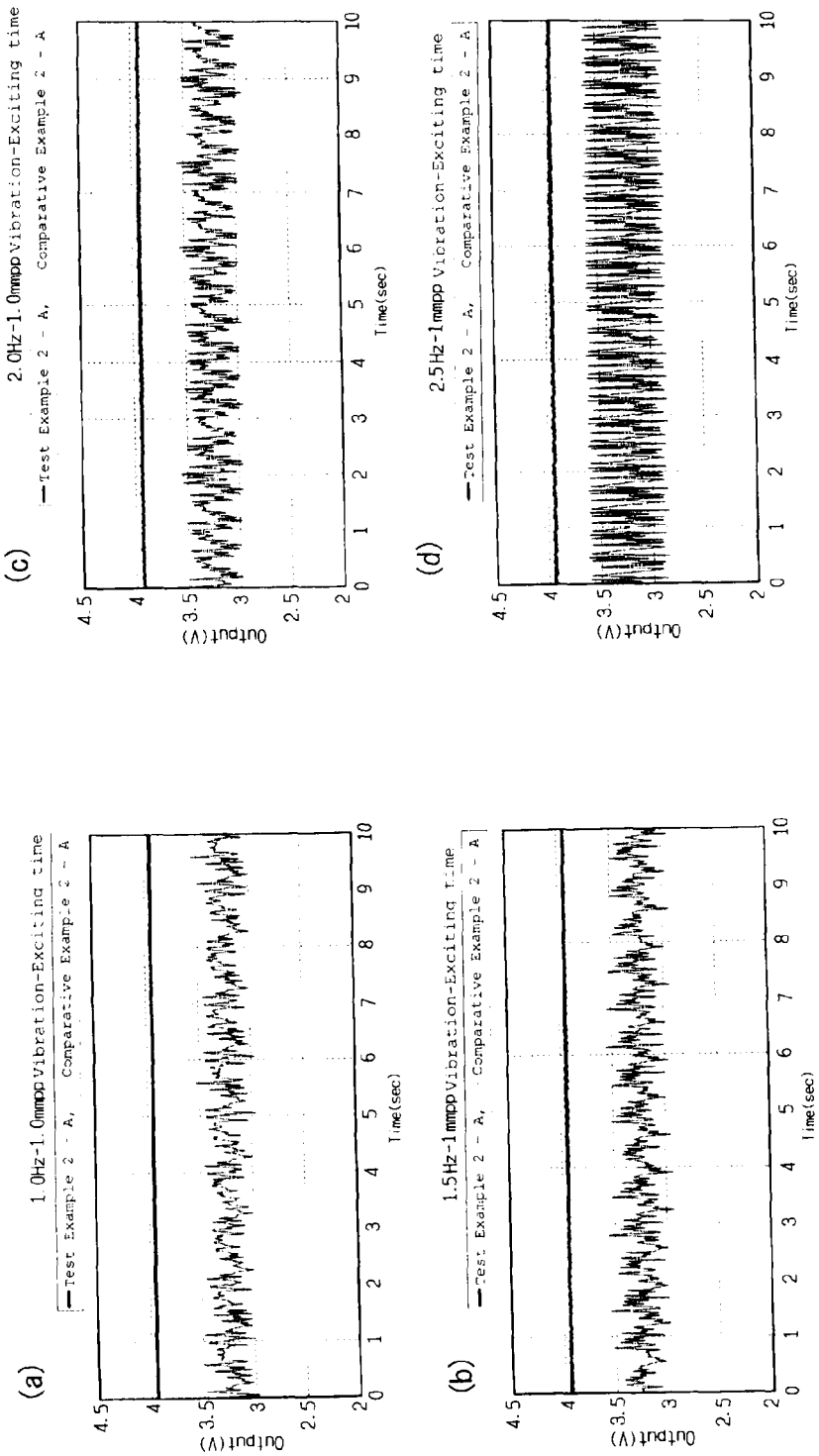
FIGS. 9A to 9D are graphs showing outputs of a sensor when vibration excitation is performed at a frequency of 1.0 Hz to 2.5 Hz in Test Example 2.
Figure 10:
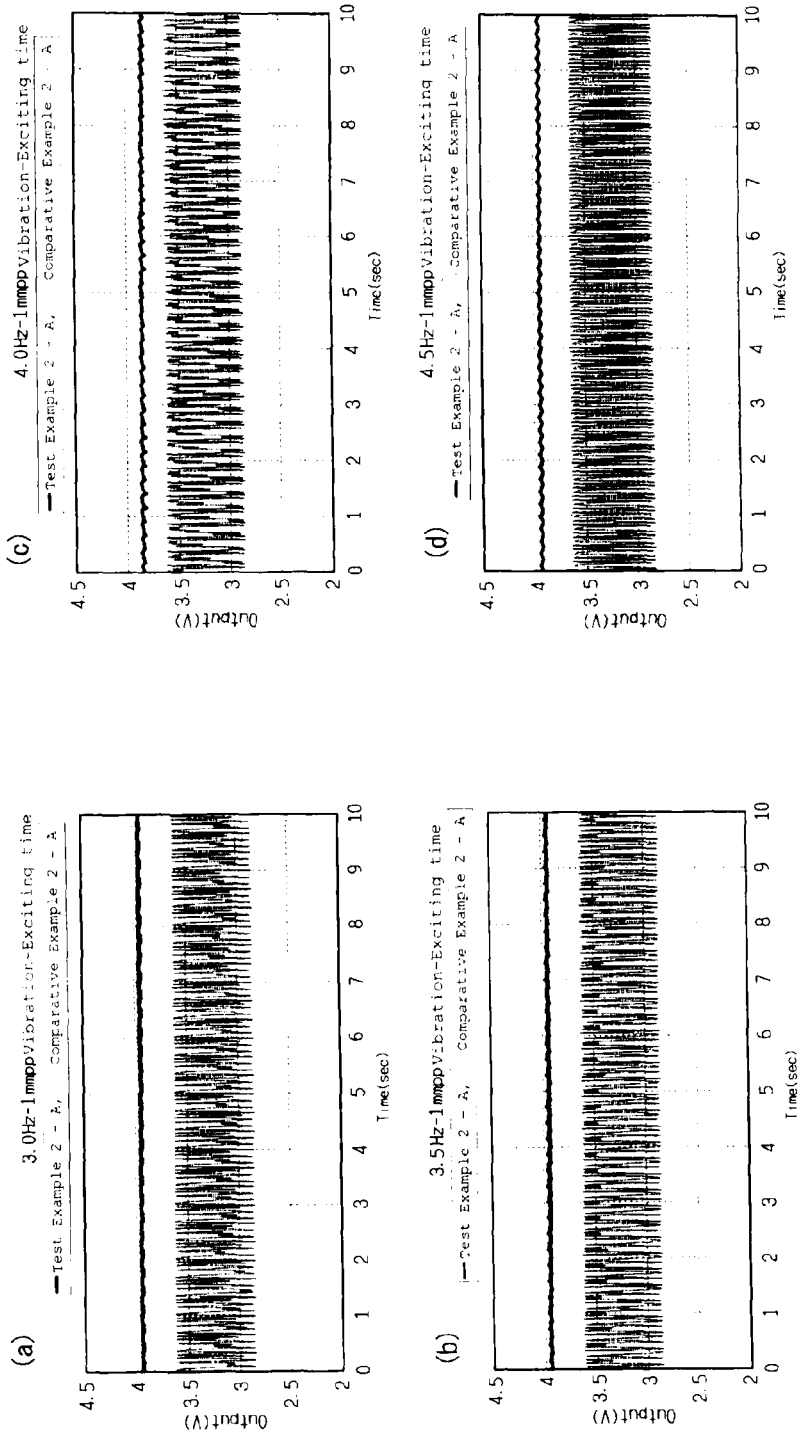
FIGS. 10A to 10D are graphs showing outputs of a sensor when vibration excitation is performed at a frequency of 3.0 Hz to 4.5 Hz in Test Example 2.
Figure 11:
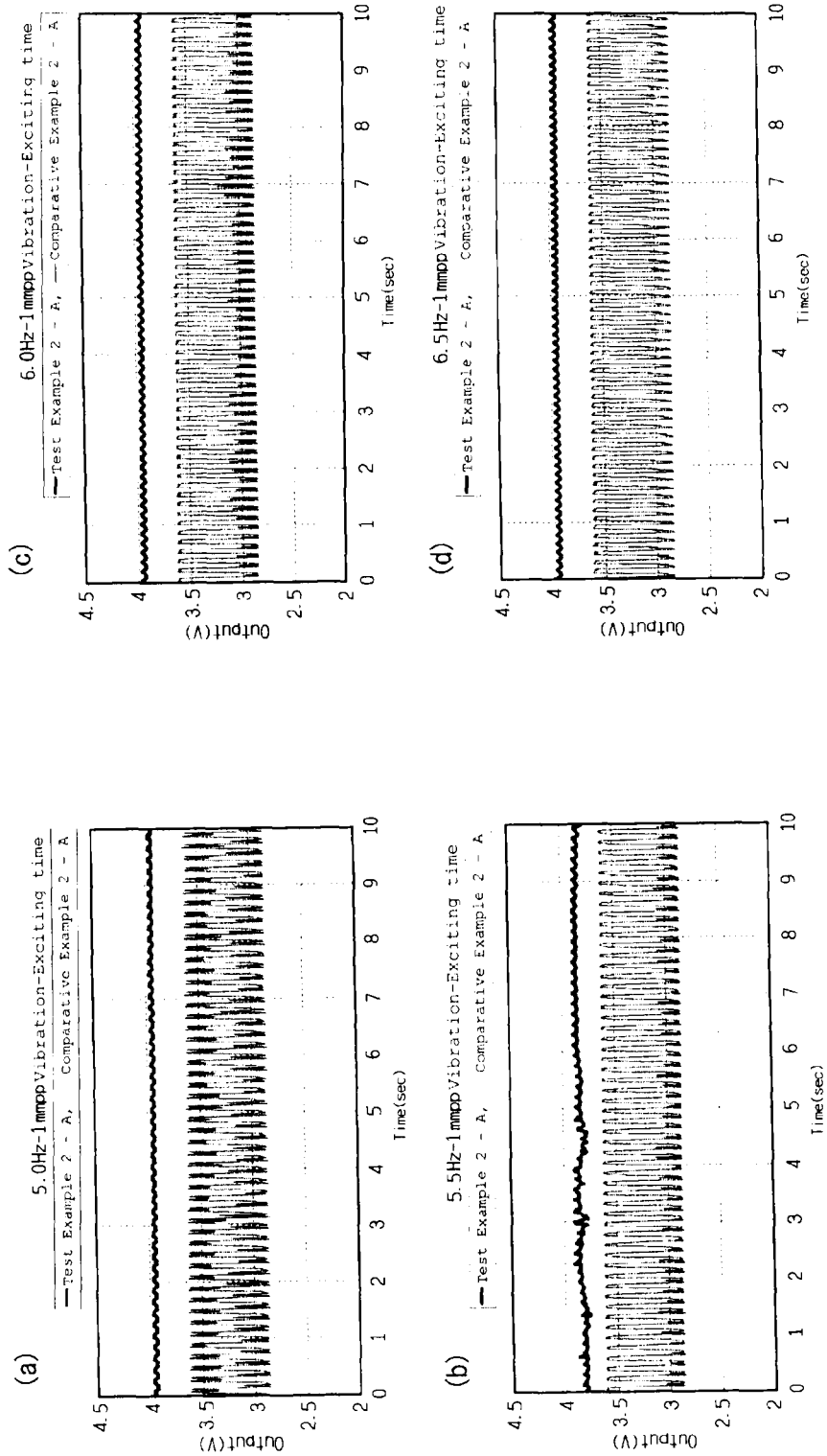
FIGS. 11A to 11D are graphs showing outputs of a sensor when vibration excitation is performed at a frequency of 5.0 Hz to 6.5 Hz in Test Example 2.
Figure 12:
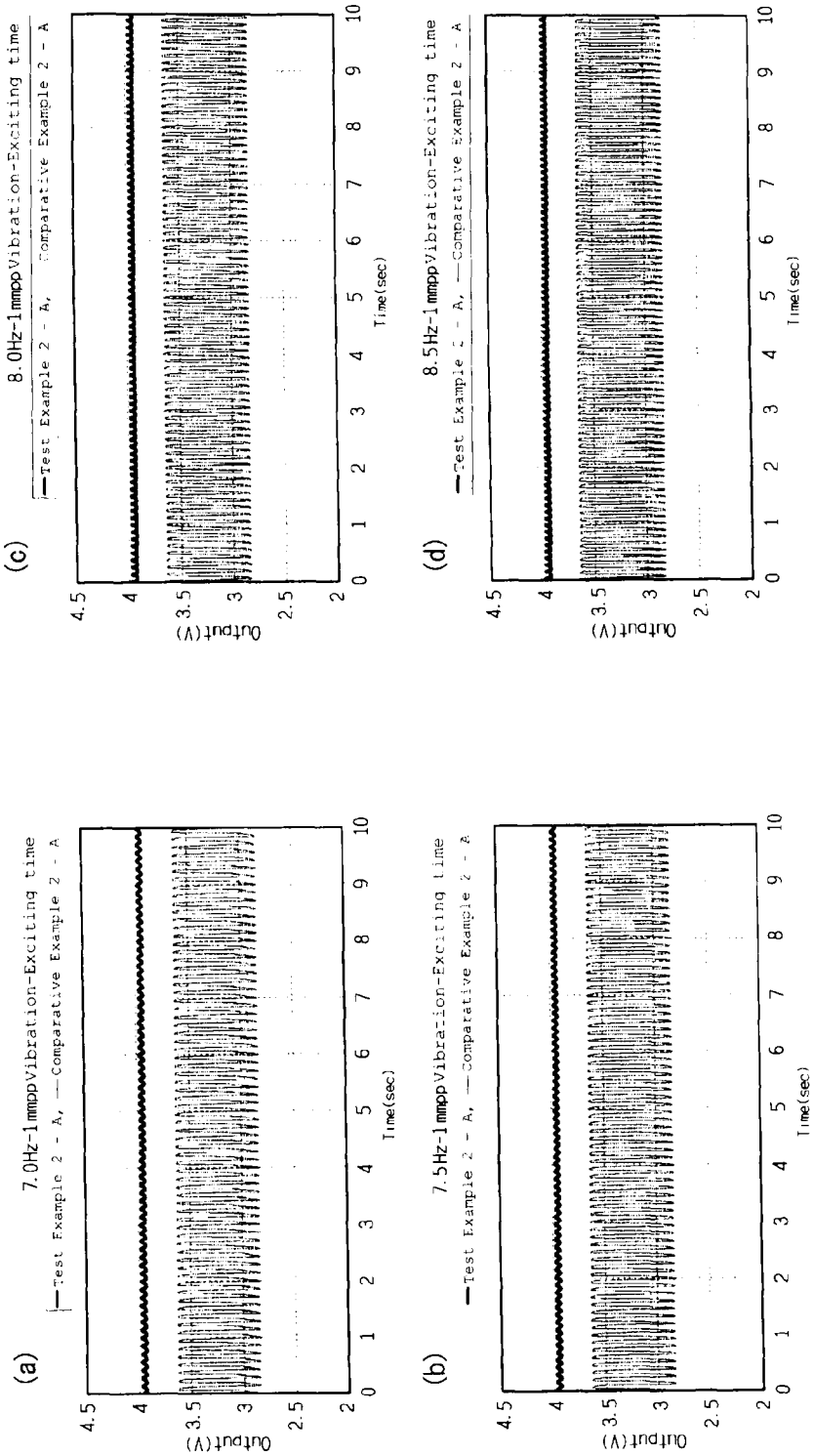
FIGS. 12A to 12D are graphs showing outputs of a sensor when vibration excitation is performed at a frequency of 7.0 Hz to 8.5 Hz in the Test Example 2.
Figure 13:
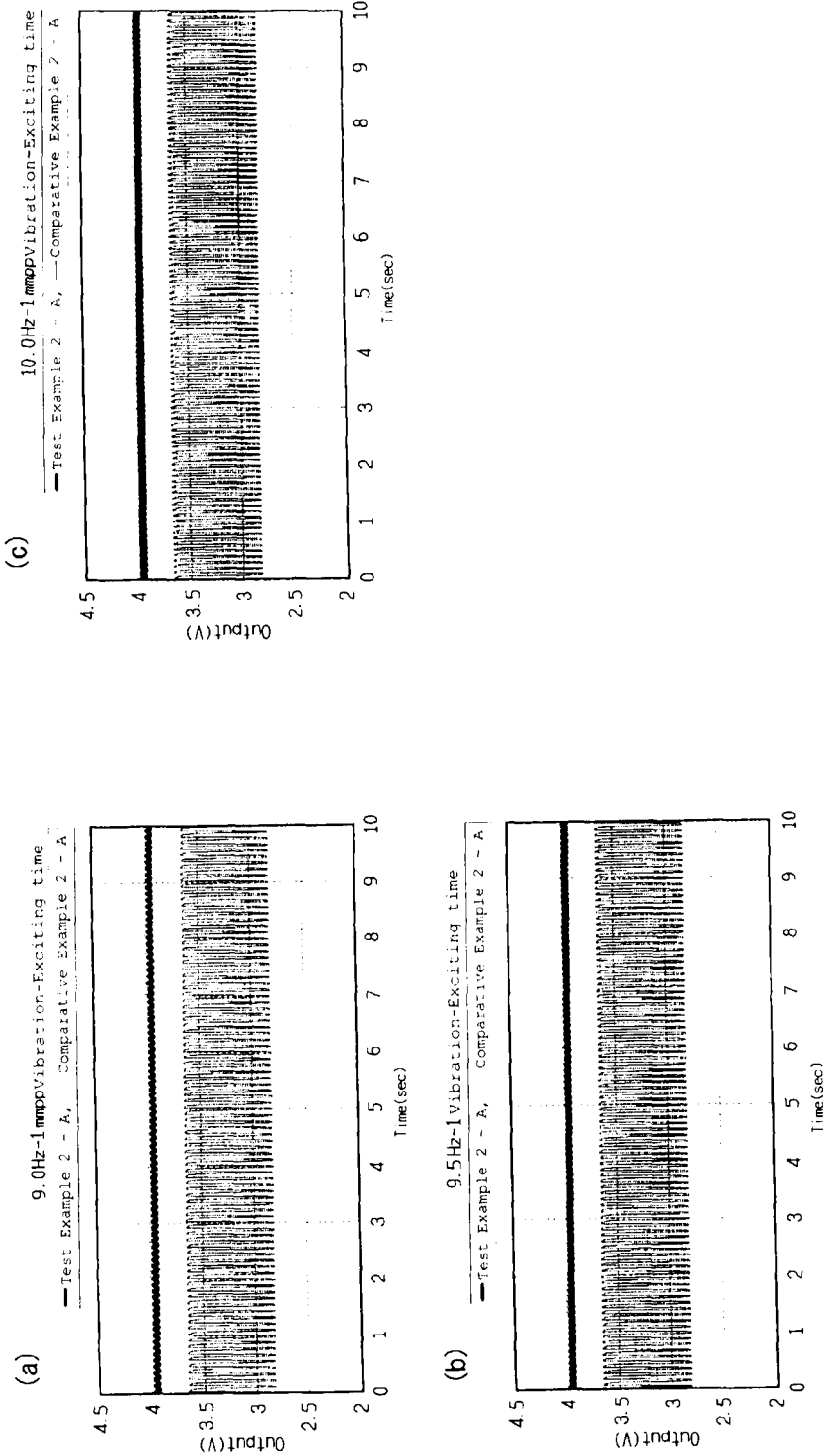
FIGS. 13A to 13C are graphs showing outputs of a sensor when vibration excitation is performed at a frequency of 9.0 Hz to 10.0 Hz in Test Example 2.

As shown in FIG. 8, regarding the receiving body 15 holding the air cushions 10 (the air cushion unit 100, the same structure and size as those in Test Example 1) was placed on a vibrating stand of a vibration exciter, and the second elastic member made of expanded resin beads 30 and the first elastic member made of expanded resin beads 20 were further stacked on an upper face thereof in this order (a stacking state of the second elastic member made of expanded resin beads 30 and the first elastic member made of expanded resin beads 20 is displayed as "a buffer" in FIG. 8) (the same aspect as "A+B+air pack" in FIG. 7), a weight of 2 kg was placed on the first elastic member made of expanded resin beads 20 and vibration excitation with an amplitude of 1 mm was performed over a frequency range of 1.0 Hz to 10 Hz at intervals of 0.5 Hz (Test Example 2-A). Further, instead of the receiving body 15 holding the air cushions 10, one small airbag 111 was placed on the vibrating stand, the second elastic member made of expanded resin beads 30 and the first elastic member made of expanded resin beads 20 were stacked thereon in this order, a weight of 2 kg was put on the first elastic member made of expanded resin beads 20, and vibration excitation was similarly performed (Comparative Example 2-A). Incidentally, PEN films were caused to adhere to the face of the first elastic member made of expanded resin beads 20 opposed to the skin member 511 and the face of the second elastic member made of expanded resin beads 30 opposed to the air cushion unit 100, respectively. Regarding the respective Examples, output voltages of the sensors 111b (capacitive microphone sensors) provided in the small airbags 111 were measured. The results were shown in FIG. 9 to FIG. 13.

From FIG. 9 to FIG. 13, in the case of Test Example 2-A, change of the output voltage hardly occurs at any frequency from 1.0 Hz to 10 Hz, but the change of the output voltage is relatively larger in the case of Comparative Example 2-A than in the case of Test Example 2-A. Therefore, by adopting the configuration in Test Example 2-A, influence of external vibrations from the seatback section 510 to the output voltage becomes considerably small. On the other hand, a biological signal inputted from the side of the first and second elastic members made of expanded resin beads 20 and 30 can be captured as change of the output voltage by the sensor 111b as Test Example 3 described later.

Test Example 3

Influence of Disturbance Vibration and Detection of Biological Signal

Figure 14:
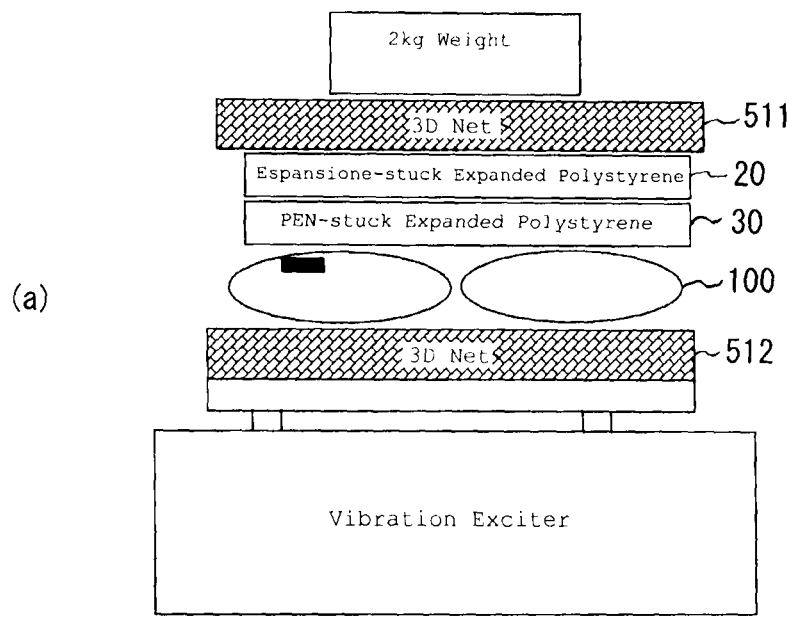
FIGS. 14A and 14B are diagrams for explaining a test method for Test Example 3.
Figure 14:
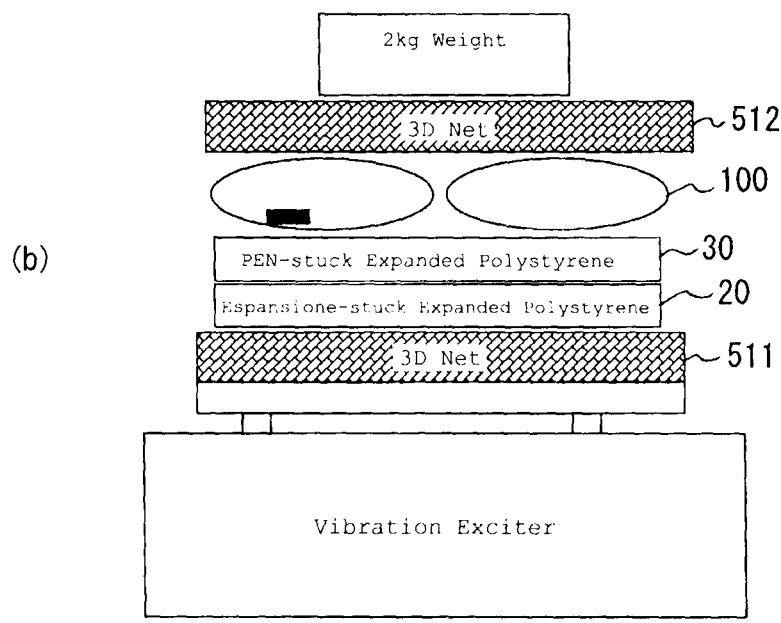

As shown in FIG. 14A, a three-dimensional solid knitted fabric (3-D net) corresponding to the cushion supporting member 512 in the seatback section 510, the receiving body 15 holding the air cushions 10 (the air cushion unit 100, the same structure and size as those of the air cushion unit 100 in Test Example 1), the second elastic member made of expanded resin beams 30, the first elastic member made of expanded resin beams 20, a three-dimensional solid knitted fabric (3-D net) corresponding to the skin member 511 in the seatback section 510 were sequentially stacked on a vibrating stand of a vibration exciter, a weight of 2 kg was placed thereon, and application of vibrations with an amplitude of 1 mm was performed at frequencies of 1.0 Hz, 1.5 Hz and 2.0 Hz close to the frequency of pulse waves of an aorta. FIG. 14A is for examining influence of disturbance vibrations received when the biological signal measuring device 1 of this embodiment has been actually assembled into the seatback section 510 in a configuration where vibrations are inputted from the side of cushion supporting member 512.

On the other hand, FIG. 14B shows a case where the respective members have been arranged in the order reversed to the arrangement order of the respective members in FIG. 14A. That is, a three-dimensional solid knitted fabric (3-D net) corresponding to the skin member 511 in the seatback section 510, the first elastic member made of expanded resin beams 20, the second elastic member made of expanded resin beams 30, the receiving body 15 holding the air cushions 10 (the air cushion unit 100 having the same structure and size as those of the air cushion unit 100 in Test Example 1), and a three-dimensional solid knitted fabric (3-D net) corresponding to the cushion supporting member 512 in the seatback section 510 were sequentially stacked on the vibrating stand. By applying vibrations in this state, a detection sensitivity of pulse waves of an aorta of the dorsal region of a person inputted from the side of the skin member 511 can be examined. Incidentally, the reason why the weight is set to 2 kg is that, when a person sits on the seat, a load from the lumbar area of the person acting on the seatback section 510 where the air cushion unit 100 is arranged corresponds to 2 kg per an area defined by a circle with a diameter of 98 mm.

Figure 15:
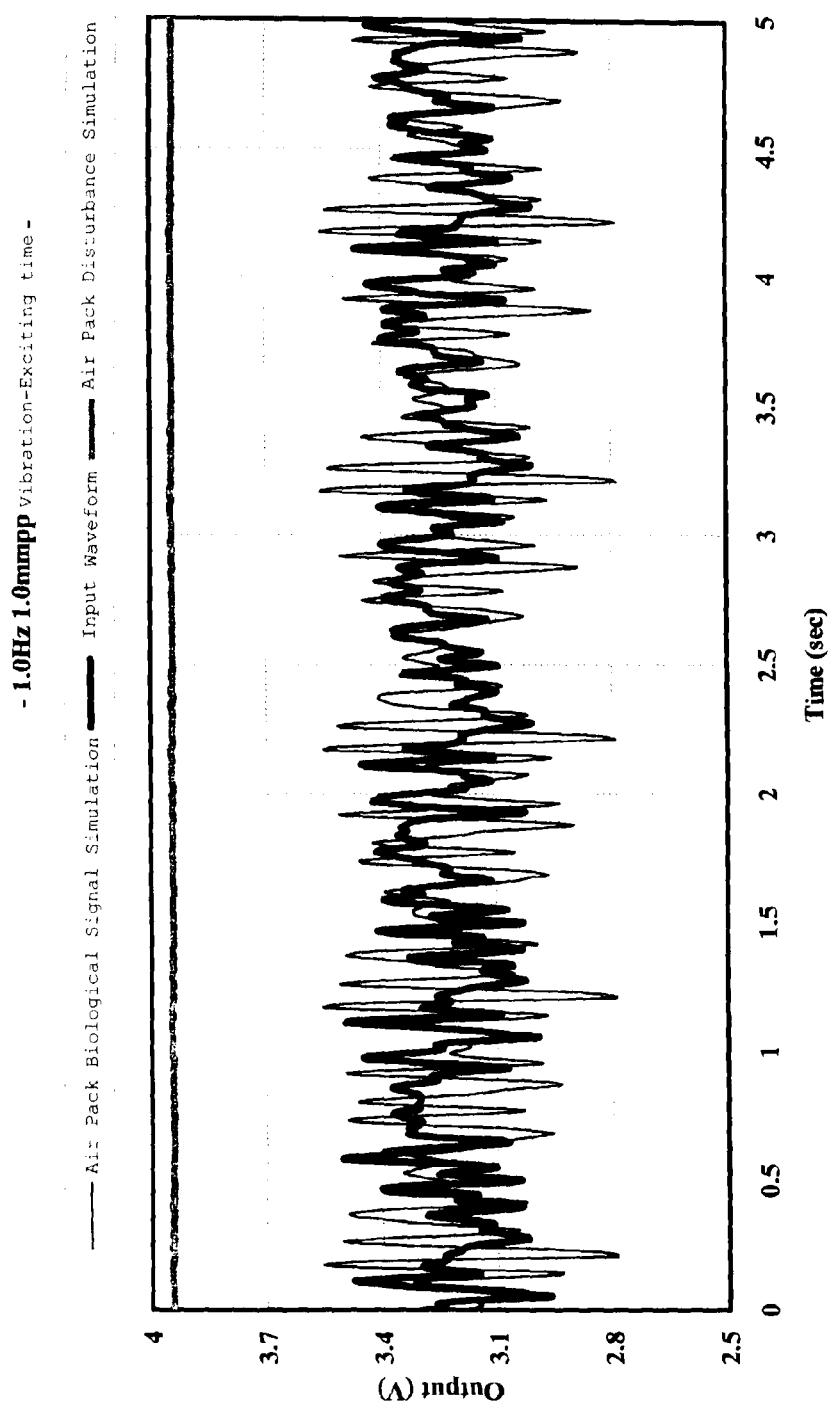
FIG. 15 is a graph showing an output of a sensor when vibration excitation is performed at a frequency of 1.0 Hz in Test Example 3.
Figure 16:
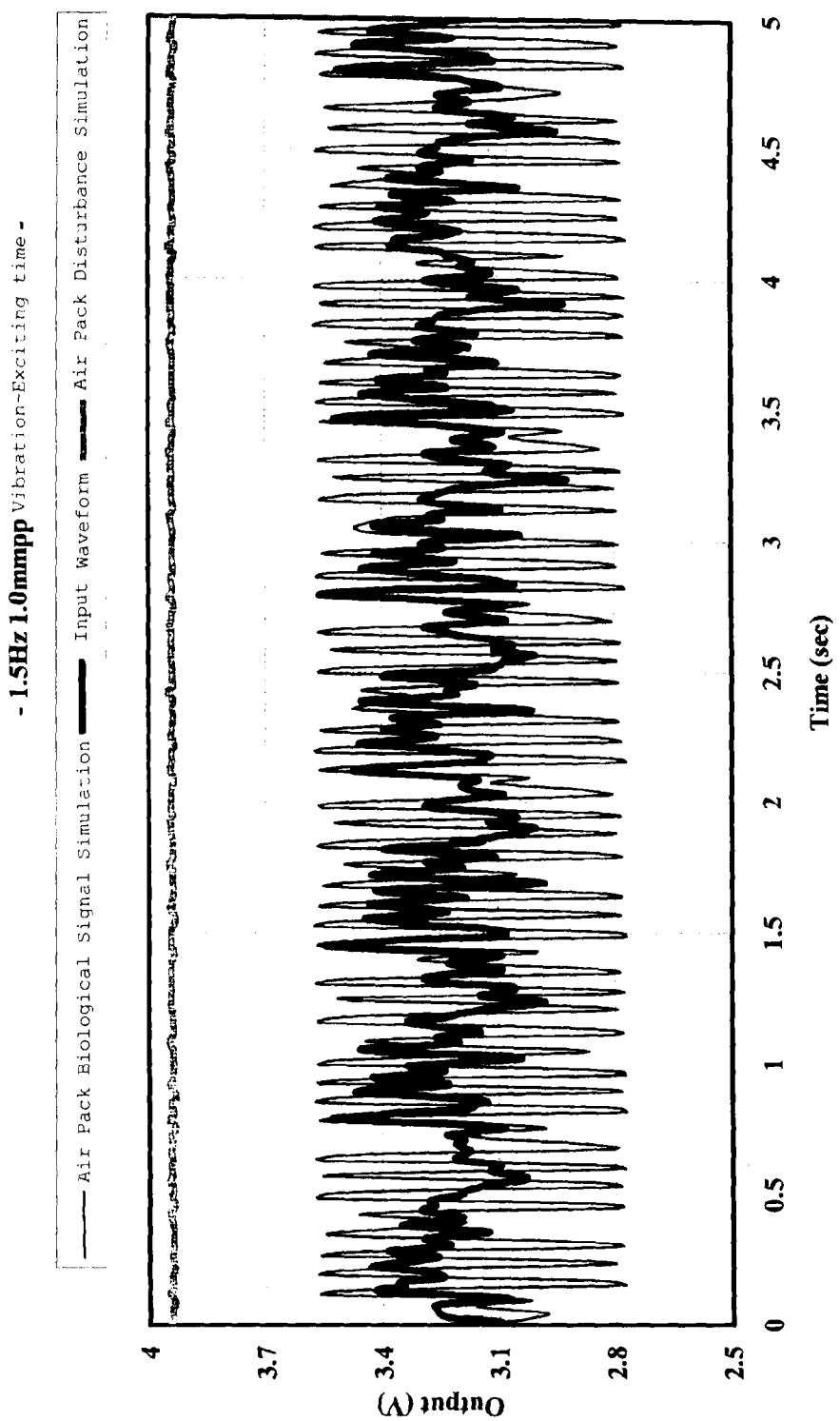
FIG. 16 is a graph showing an output of a sensor when vibration excitation is performed at a frequency of 1.5 Hz in Test Example 3.
Figure 17:
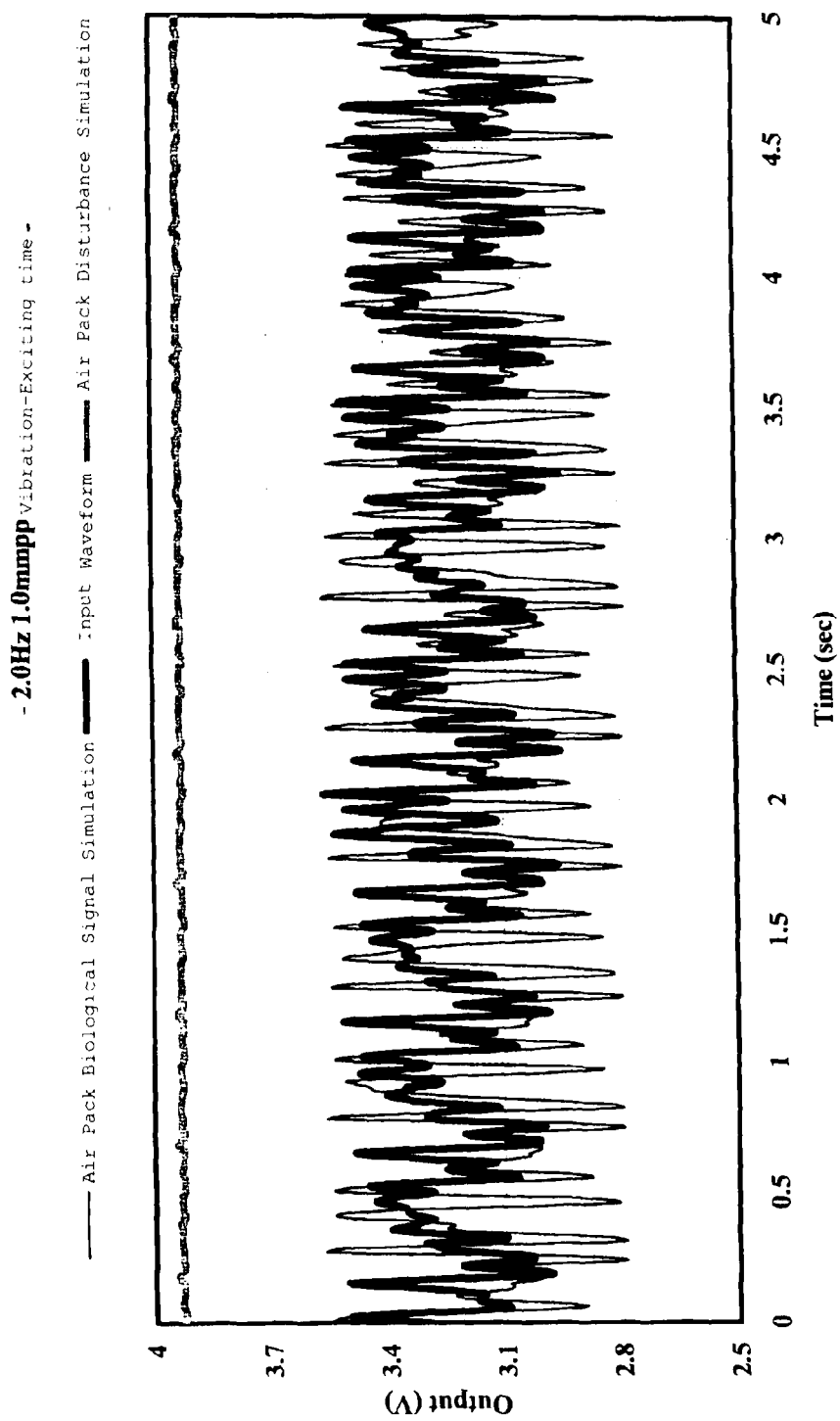
FIG. 17 is a graph showing an output of a sensor when vibration excitation is performed at a frequency of 2.0 Hz in Test Example 3.
Figure 18:
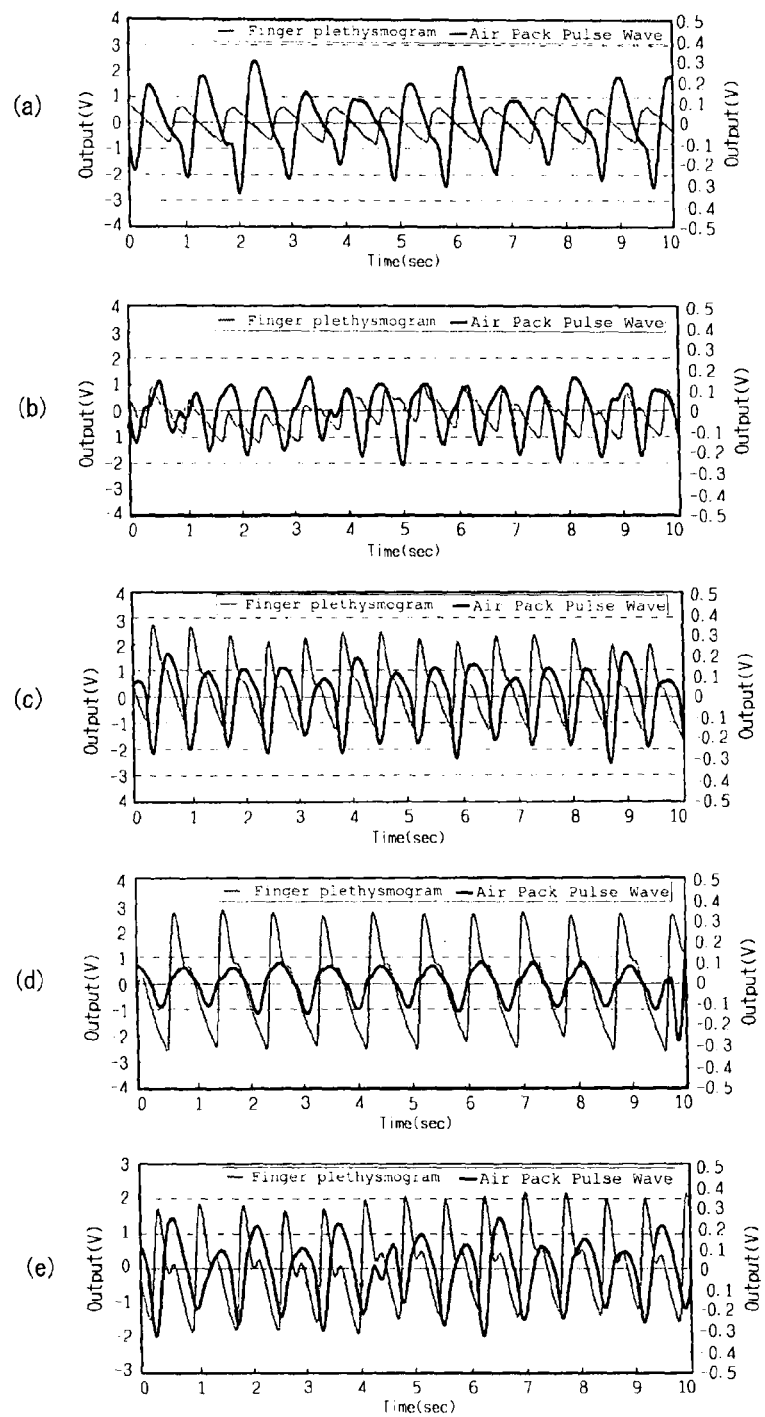
FIGS. 18A to 18E are graphs showing time series waveforms of pulse waves of aortas of dorsal regions of five subjects (air pack pulse waves) and finger plethysmograms thereof in Test Example 4.
Figure 19:
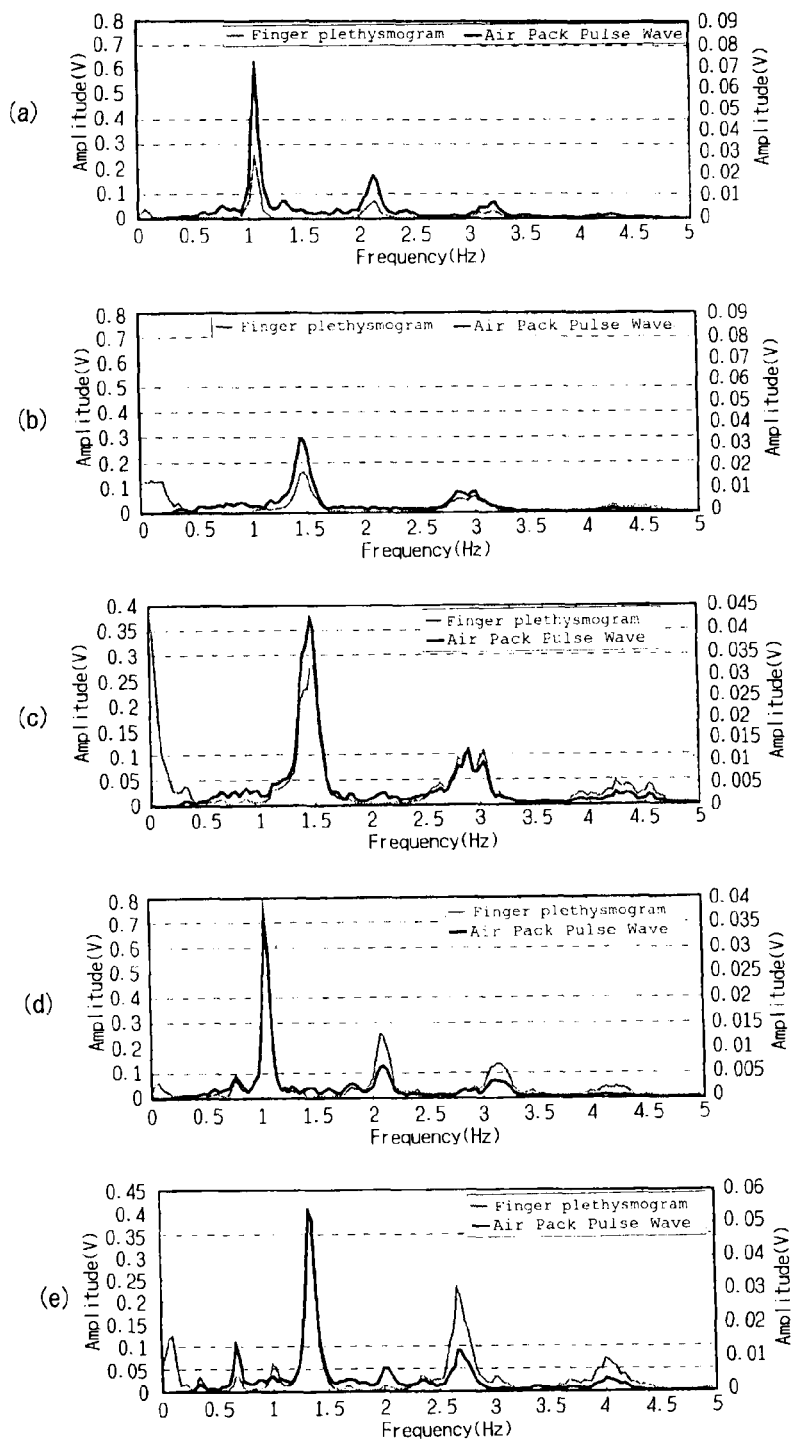
FIGS. 19A to 19E are graphs showing respective frequency analysis results of FIGS. 18A to 18E.

The results are shown in FIG. 15 to FIG. 17. In these figure, "air pack disturbance simulation" is a result obtained in FIG. 14A, while "air pack biological signal simulation" is a result obtained in FIG. 14B. Input waveforms of a vibration exciter are also shown. From these figures, it is understood that "air pack disturbance simulation" shows a state close to a straight line which hardly involve amplitude and almost all of disturbance vibrations has been eliminated. On the contrary, it is understood that "air pack biological signal simulation" shows an amplified waveform beyond an input waveform. From this fact, it can be said that pulse waves of aorta of a dorsal close to a range of 1.0 Hz to 2.0 Hz can be detected securely even under a dynamic condition where disturbance vibrations are inputted, such as a riding time, without burying the pulse wave into the disturbance vibrations.

Test Example 4

Measurement of Biological Signal

As shown in FIG. 2, the receiving body 15 holding the air cushions 10 (the air cushion unit 100 having the same structure and size as those of the air cushion unit 100 in Test Example 1), the second elastic member made of expanded resin beams 30, and the first elastic member made of expanded resin beams 20, which were explained in the above embodiment, were sequentially received in the seatback section 510 of the seat 500. Incidentally, the skin member 511 used in the seatback section 510 is a three-dimensional solid knitted fabric (Product Number 49013D produced by Suminoe Textile Co., Ltd.). Further, assembling of the central small air airbag 111 (width of 60 mm and length of 160 mm) provided with the sensor 111b and configuring the air cushion 10 on the left side of a seat-sitting person into the seatback section 510 was performed such that the intersecting portion P of one of side edges of the central small airbag 111 closer to the center of the seatback section 510 and a lower edge of the central small airbag 111 was positioned such that a length from an upper face of the seat cushion section 520 along a surface of the seatback section 510 was 220 mm and a distance from the center of the seatback section 510 was 80 mm. State analyzing means 60 comprising a computer which analyzes a state of a person based upon air pressure fluctuation obtained by measuring an electric signal from the sensor 111b of the above small airbag 111 was disposed (see FIG. 1), five Japanese men in their 20s to 40s were made to sit on the seat 500, respectively, and pulse waves of aortas of their dorsal regions were collected. Further, the subjects also each wore a finger plethysmogram meter (Finger Clip Probe SR-5C manufactured by AMCO, INC.) to measure his finger plethysmogram.

FIGS. 18A to 18E show aortas pulse waves (air pack pulse waves) of dorsal regions and time series waveforms of finger plethysmograms of five subjects, and FIGS. 19A to 19E show respective frequency-analyzed results. From these figures, it is understood that the frequencies of the air pack pulse waves coincide with those of the finger plethysmograms, and the air pack pulse wave can be captured up to their third harmonic components like the case of the finger plethysmograms. Since the first and second elastic members made of expanded resin beads 20 and 30 which are thin such as about 5 to 6 mm are small in mass, their expanded bead bodies are covered with the covering materials different in elasticity, and amplifications are performed by utilizing their spring constants, it is difficult for bubbles in the expanded bead bodies to absorb acoustic waves. It is thought that a natural vibration frequency of a stacked body of the first and second elastic members made of expanded resin beads 20 and 30 is close to 1 Hz, and it is thought that it is difficult to damp the air pack pulse waves.

Test Example 5

State Determination of Static Sitting State

A healthy Japanese man in his 30s was made to sit on the seat 500 in Test Example 4 and a catnap detecting experiment for one hour was conducted. This subject wore the same finger plethysmogram meter as that in Test Example 4 to measure his finger plethysmogram and also wore a simplified electroencephalograph (Model Number FM-515A manufactured by Futek Electronics Co., Ltd.) to measure his brain waves.

Figure 20:
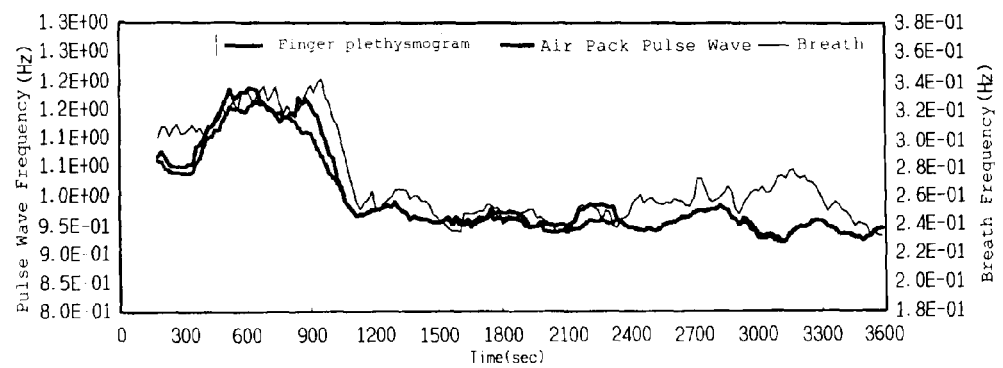
FIG. 20 is a graph showing a frequency fluctuation of the finger plethysmogram, a frequency fluctuation of the air pack pulse wave, and a frequency fluctuation of a respiratory component extracted from an electric signal of the sensor in Test Example 5.

FIG. 20 is a diagram showing a frequency fluctuation of the finger plethysmogram, a frequency fluctuation of the air pack pulse wave, and a frequency fluctuation of a respiratory component extracted from an electric signal of the sensor 111b, from which it is understood that the three frequency fluctuations coincide with each other well. In the figure, all three frequency fluctuations show a decrease tendency after 900 seconds, but it is thought that this tendency occurred due to sleepiness caused by his eye closure from 900 seconds.

Figure 21:
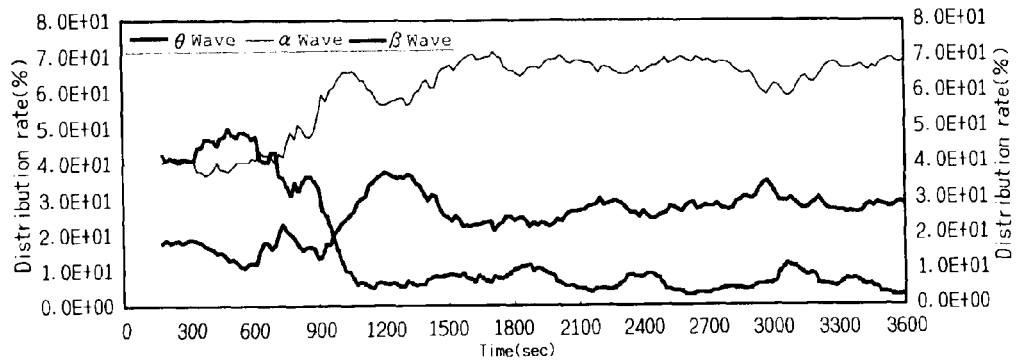
FIG. 21 is a graph showing distribution rates of α wave, β wave, and θ wave measured from a simplified electroencephalograph.

FIG. 21 shows distribution rates of $\alpha$ wave, $\beta$ wave, and $\theta$ wave measured by a simplified electroencephalograph. The $\alpha$ wave and the $\theta$ wave ascend and the $\beta$ wave descends just after his eye closure after 900 seconds. It is judged that this phenomenon is based upon the fact that he has been induced to a relaxed state by an effect of his eye closure. From such a fact that the distribution rate of the $\alpha$ wave descends and the distribution rate of the $\theta$ wave ascends near 1200 seconds, it is judged that he fell into sleep.

Figure 22:
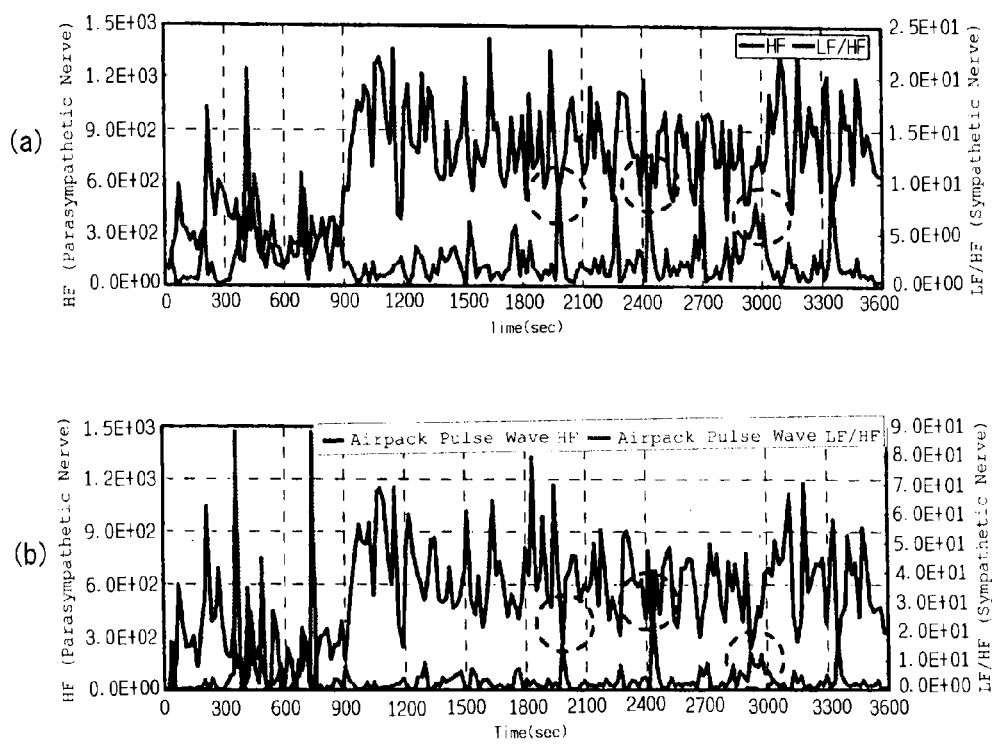
FIG. 22A is a graph showing time series fluctuations of HF component and LF/HF component of a finger plethysmogram.
FIG. 22B is a graph showing time series fluctuations of HF component and LF/HF component of an air pack pulse wave.

FIG. 22A is a graph showing time series fluctuations of a HF component and an LF/HF component of the finger plethysmogram, and FIG. 22B is a graph showing time series fluctuations of a HF component and an LF/HF component of the air pack pulse wave. The LF/HF component is an index showing a state of sympathetic nerve activity, while the HF component is an index showing parasympathetic nerve activity. In FIG. 22A, since the HF component of the finger plethysmogram ascends and the LF/HF component shows a descending tendency from 900 seconds, it can be captured that the subject moves into his sleeping state, but the HF component and the LF/HF component of the air pack pulse wave in FIG. 22B show the same tendencies as the above, from which it is understood that an aspect of a fluctuation of the autonomic nerve of the subject is captured from the air pack pulse wave. In the figures, characteristic peaks at 1900 seconds, 2400 seconds, and 3100 seconds also coincide with temporal ascending of the distribution rate of the $\beta$ wave in FIG. 21.

Figure 23:
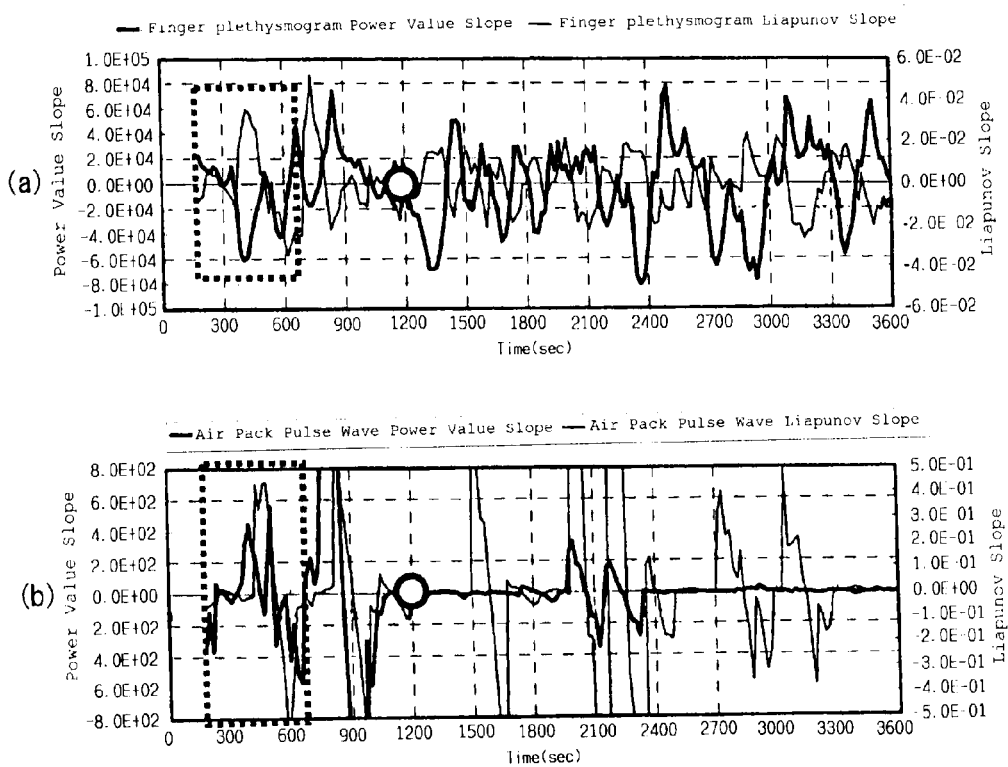
FIG. 23A is a graph showing slope time series waveforms of a power value and a maximum Liapunov index of a finger plethysmogram.
FIG. 23B is a graph showing slope time series waveforms of a power value and a maximum Liapunov index of an air pack pulse wave.

FIGS. 23A and 23B are graphs showing slope time series waveforms of the power values and the maximum Liapunov indexes of the finger plethysmogram and the air pack pulse wave.

Incidentally, calculation of the slope time series waveform of the power value and the slope time series waveform of the maximum Liapunov index were performed by utilizing the method proposed in JP-A-2004-344612 filed by the present applicant. Specifically, an electric signal from the sensor 111b in the small airbag 111 is received by the state analyzing means 60 comprising a computer. The state analyzing means 60 is set with computer programs such as power value slope calculating means, maximum Liapunov index slope calculating means, and sleep onset prediction determining means. The power value slope calculating means calculates a difference between an upper limit side peak value and a lower limit side peak value for each predetermined time range from peak values of each cycle of a time series waveform of a signal received from the sensor 111b to utilize the difference as a power value, thereby obtaining time series data of the power value and performing slide calculation by a predetermined number of times to obtain a slope to a time axis in the predetermined time range of the power value. More specifically, the power value slope calculating means obtains the maximum value and the minimum value by applying a smoothing differentiation according to Savitzky and Golay to the time series waveform of a signal received from the sensor 111b. The power value slope calculating means distinguishes the maximum value and the minimum value from each other for each 5 seconds to obtain average values thereof. The power value slope calculating means uses square of a difference between the average values of the maximum value and the minimum value obtained as the power value to plot the power value for each 5 seconds, thereby producing a time series waveform of the power value. The power value slope calculating means applies least-square method to a certain time width Tw (180 seconds) to obtain a slope of the power value in order to read global change of the power value from the time series waveform. Next, the power value slope calculating means similarly calculates the next time width Tw at an overlap time TI (162 seconds) to plot the result. The slope time series waveform of the power value is obtained by repeating this calculation (slide calculation) sequentially.

The maximum Liapunov index calculating means obtains time series data of the maximum Liapunov index from the time series waveform of the signal received from the sensor 111b, and performs slide calculation by a predetermined number of times to obtain a slope to the time axis in the predetermined time range of the maximum Liapunov index. That is, after applying chaos analysis to the time series waveform to calculate the maximum Liapunov index, the maximum Liapunov index calculating means obtains the maximum value and the minimum value by performing smoothing differentiation like the above to obtain the slope time series waveform by performing slide calculation.

The sleep onset prediction determining means superimposes the respective slope time series waveforms obtained by the above-described power value slope calculating means and maximum Liapunov index slope calculating means to determine waveforms satisfying a relationship where two slope time series waveforms have opposite phases to each other as a sleep onset prediction signal. Preferably, regarding the two slope time series waveforms, the sleep onset prediction determining means determines whether or not a low-frequency waveform with large amplitude occurred in the slope time series waveform of the power value and waveforms where the slope time series waveform of the power value and the slope time series waveform of the maximum Liapunov index had opposite phases to each other occurred. As viewing FIGS. 23A and 23B, there is a sleep onset prediction signal in the vicinity of about 400 seconds to about 450 seconds in these figures, and the subject enters a sleep onset point in the vicinity of 1200 seconds where the amplitude becomes small. Accordingly, it is understood that the sleep onset prediction can be determined from a pulse wave of an aorta of a dorsal region like the finger plethysmogram.

(State Determination of Dynamic State)

Figure 27:
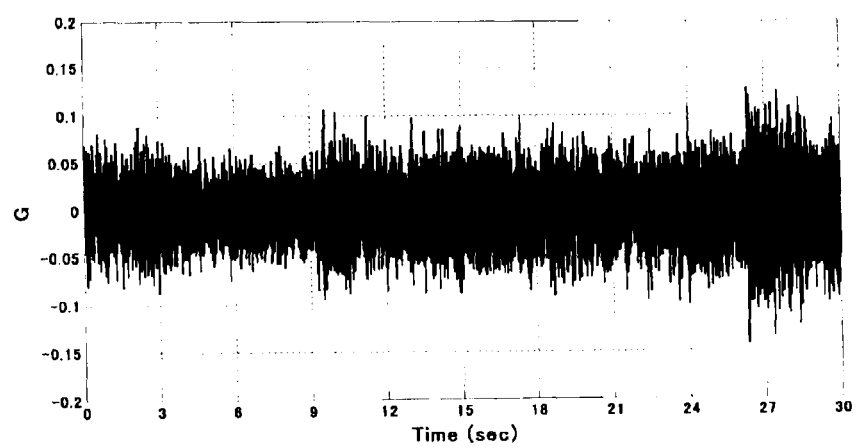
FIG. 27 is a graph showing a vibration waveform when vibration excitation is performed by a vibration exciter.

The seat 500 in Test Example 4 was set on a vibration exciter, a healthy Japanese man in his 30s was made to sit on the seat 500, and a catnap detecting experiment for 30 minutes was performed. A vibration-exciting waveform at this experiment is a waveform obtained by compressing acceleration data in a small-sized minivan at a speed of 60 km/h on a vehicle road during running to half thereof and shown in FIG. 27. The experiment was performed with the subject with his eye-closure from 900 seconds like Test Example 5. This subject also wore the same finger plethysmogram meter as that in Test Example 4 to measure his finger plethysmogram.

Figure 24:
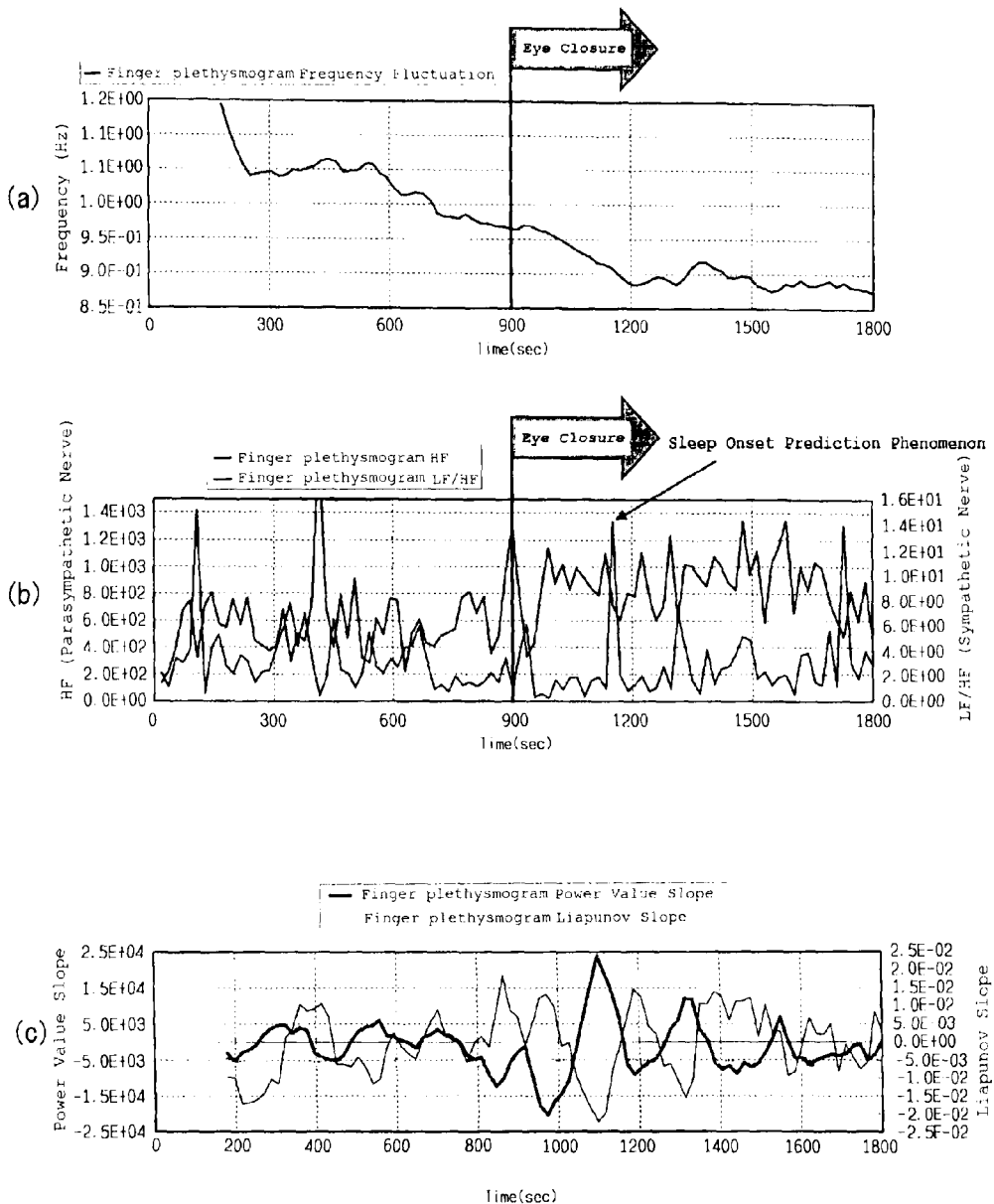
FIG. 24A is a graph showing a frequency fluctuation of a finger plethysmogram in Test Example 6.
FIG. 24B is a graph showing time series fluctuations of HF component and LF/HF component of the finger plethysmogram.
FIG. 24C is a graph showing slope time series waveforms of a power value and a maximum Liapunov index of the finger plethysmogram.

FIG. 24A is a graph showing a frequency fluctuation of a finger plethysmogram, from which it is understood that large decrease occurred after 900 seconds at which the subject closed his eyes. FIG. 24B is a graph showing time series fluctuations of a HF component and a LF/HF component of a finger plethysmogram. In FIG. 24B, since the HF component of the finger plethysmogram ascends and the LF/HF component shows a descending tendency from 900 seconds, it can be captured that the subject moved into his sleeping state. In the LF/HF component, it is thought that a characteristic peak first appearing just before 1200 seconds after the descending tendency was shown was a sleep onset prediction phenomenon. FIG. 24C is a graph showing slope time series waveforms of the power value and the maximum Liapunov index of the finger plethysmogram obtained by a calculating method similar to that in Test Example 4. In FIG. 24C, a low-frequency waveform with large amplitude occurs in the slope time series waveform of the power value and there are waveforms where the slope time series waveform of the power value and the slope time series waveform of the maximum Liapunov index have opposite phases to each other for a period from 900 seconds to 1200 seconds, from which it is understood that a sleep onset prediction phenomenon occurred at this time point.

Figure 25:
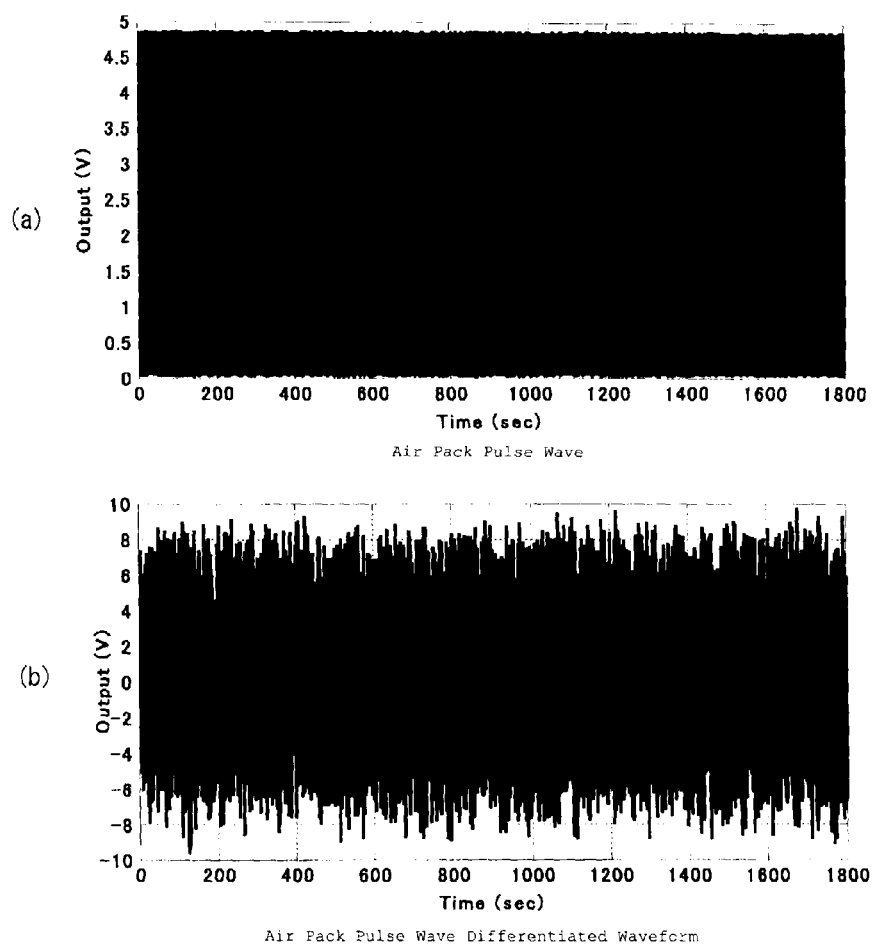
FIG. 25A is a graph showing an original waveform of an air pack pulse wave in Test Example 6.
FIG. 25B is a graph showing a differentiated waveform of the original waveform.
Figure 26:
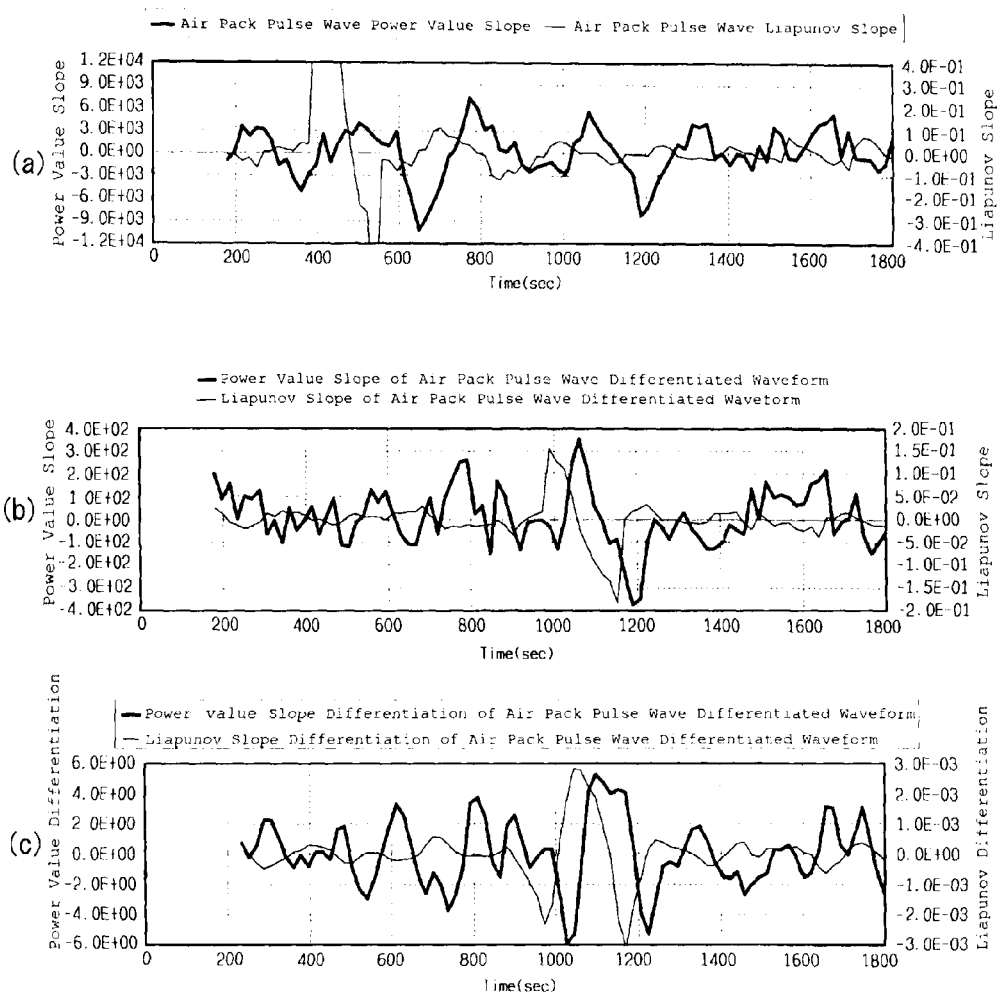
FIG. 26A is a graph showing slope time series waveforms of the power value and the maximum Liapunov index obtained from the original waveform of the air pack pulse wave shown in FIG. 25A.
FIG. 26B is a graph showing slope time series waveforms of the power value and the maximum Liapunov index obtained from the differentiated waveform of the air pack pulse wave shown in FIG. 25B.
FIG. 26C is a graph showing differentiated waveforms of the slope time series waveforms shown in FIG. 26B.

On the other hand, FIG. 25A shows an original waveform of an air pack pulse wave, and slope time series waveforms of the power value and the maximum Liapunov index obtained from the original waveform of the air pack pulse by the power value slope calculating means and the maximum Liapunov index slope calculating means are shown in FIG. 26A. According to the analysis results of the finger plethysmogram shown in FIGS. 24A to 24C, it is thought that the sleep onset prediction phenomenon occurred for the period from 900 seconds to 1200 seconds, as described above, but it is unclear in the slope time series waveforms of the power value and the maximum Liapunov index of the air pack pulse wave shown in FIG. 26A whether or not the characteristic waveform of the sleep onset prediction phenomenon occurred for the period from 900 seconds to 1200 seconds.

Therefore, it is preferred that a configuration where the state analyzing means 60 is provided with differentiated waveform calculating means which differentiates a time series waveform (original waveform) of the output signal obtained from the sensor 111b to obtain a differentiated waveform is adopted. It is further preferred that a configuration provided with slope time series differentiated waveform calculating means which further differentiates the power value slope time series waveform and the maximum Liapunov index slope time series waveform obtained by the power value slope calculating means and the maximum Liapunov index slope calculating means to obtain differentiated waveforms of respective slope time series waveforms is adopted.

As shown in FIG. 25B, the differentiated waveform calculating means obtains a differentiated waveform obtained by differentiating the original waveform of the air pack pulse wave. The power value slope calculating means and the maximum Liapunov index slope calculating means obtain slope time series waveforms of the power value and the maximum Liapunov index by using the air pack pulse wave differentiated waveform as shown in FIG. 26B. According to FIG. 26B, it is understood that a low-frequency waveform with large amplitude occurred in the slope time series waveform of the power value and there is waveforms where the slope time series waveform of the power value and the slope time series waveform of the maximum Liapunov index had opposite phases to each other for a period from 900 seconds to 1200 seconds.

The slope time series differentiated waveform calculating means further differentiates the slope time series waveforms of the power value and the maximum Liapunov index shown in FIG. 26b to obtain waveforms shown in FIG. 26C. According to FIG. 26C, it is understood that influence of a high-frequency signal remaining in FIG. 26B can be reduced and the differentiated waveforms further approach the slope time series waveforms of the power value and the maximum Liapunov index of the finger plethysmogram, so that the state determination utilizing the air pack pulse wave can be performed more accurately in a dynamic state.

Here, the differentiated waveform shown in FIG. 25B is data obtained by applying a first order differentiation to the original waveform shown in FIG. 25A by the differentiated waveform calculating means. Further, the differentiated waveforms shown in FIG. 26C are data obtained by applying a first order differentiation to the respective slope time series waveforms of the power value and the maximum Liapunov index shown in FIG. 26B by the slope time series differentiated waveform calculating means. That is, the respective differentiated waveforms are obtained by applying the first order differentiation to the original waveform or the slope time series waveforms to be differentiated, but such a configuration can be adopted that differentiated waveforms are obtained by performing second order differentiation both in the differentiated waveform calculating means and in the slope time series differentiated waveform calculating means. By performing differentiation processing, high-frequency components in the original waveform and the slope time series waveform to be differentiated are emphasized, so that the differentiated waveforms approach the time series waveform of the finger plethysmogram which is a peripheral pulse wave, but the first order differentiation and the second order differentiation are different in degree of emphasis from each other, determination about which result comes closer to the time series waveform of the finger plethysmogram cannot be made clearly depending on the shape of the original waveform of a pulse wave or a level of a high-frequency component contained in the pulse wave, where differences among individuals are present. That is, there are a case (a person) where a differentiated waveform approaching the time series waveform of the finger plethysmogram is obtained by performing first order differentiation in both the differentiated waveform calculating means and the slope time series differentiated waveform calculating means, a case (a person) where a differentiated waveform approaching the time series waveform of the finger plethysmogram is obtained by performing second order differentiation in both the differentiated waveform calculating means and the slope time series differentiated waveform calculating means, and a case (a person) where a differentiated waveform approaching the time series waveform of the finger plethysmogram is obtained by performing calculation processing of first order differentiation in one of the differentiated waveform calculating means and the slope time series differentiated waveform calculating means and performing calculation processing of second order differentiation in the other. Therefore, regarding determination about which calculating processing can obtain a differentiated waveform coming closer to the time series waveform of the finger plethysmogram, it is preferred that a learning function using a neural network where a combination capable of performing processing using both calculation results of first order differentiation and second order differentiation for each riding on an automobile for an initial duration of several days and comparing the processed data with the time series waveform of the finger plethysmogram preliminarily stored to calculate a tendency coming closer to the time series waveform of the finger plethysmogram can be automatically set in the differentiated waveform calculating means and the slope time series differentiated waveform calculating means is provided.

Incidentally, in the above embodiment, the air cushions 10 and the first and second elastic members made of expanded resin beads 20 and 30 are assembled into the seat for an automobile serving as the human body supporting means, but they can be assembled into bedclothes such as a bed, a chair for diagnosis in hospital facility, or the like, serving as the human body supporting means.

REFERENCE SIGNS LIST

1: biological signal measuring device
10: air cushion
11: surface side air cushion
111: small airbag
111b: sensor
112: three-dimensional solid knitted fabric
12: back side air cushion
121: large airbag
122: three-dimensional solid knitted fabric
15: receiving body
100: air cushion unit
20: first elastic member made of expanded resin beads
30: second elastic member made of expanded resin beads
40, 45: three-dimensional solid knitted fabric
60: state analyzing means
500: seat
510: seatback section
511: skin member
512: cushion supporting member
520: seat cushion section

The invention claimed is:

1. A biological signal measuring device comprising:
an air cushion provided with an airbag and a sensor which detects air pressure fluctuation of the airbag according to load fluctuation, wherein the air cushion is assembled between a skin member and a cushion supporting member arranged on a back face side of the skin member at a site supporting at least the vicinity of a lumbar area of a person, wherein
an elastic member made of expanded resin beads which has a size covering the air cushion is disposed between the skin member and the air cushion and is configured by stacking a first elastic member made of expanded resin beads and a second elastic member made of expanded resin beads to each other, and each of the first elastic member made of expanded resin beads and the second elastic member made of expanded resin beads comprises an expanded bead body and a covering material covering an outer face of the expanded bead body.

2. The biological signal measuring device according to claim 1, wherein the covering material covering the expanded bead body configuring one of the first elastic member made of expanded resin beads and the second elastic member made of expanded resin beads is different in retractility from the covering material covering the expanded bead body configuring the other.

3. The biological signal measuring device according to claim 2, wherein the covering material covering the expanded bead body configuring one of the first elastic member made of expanded resin beads and the second elastic member made of expanded resin beads is an elastic fiber nonwoven fabric formed by melting and bonding thermoplastic elastomer elastic fibers mutually, and the covering material covering the expanded bead body configuring the other is a nonwoven fabric made of thermoplastic polyester having smaller in retractility than the elastic fiber nonwoven fabric.

4. The biological signal measuring device according to claim 3, wherein polyester films are stuck to a surface of the first elastic member made of expanded resin beads and a back face of the second elastic member made of expanded resin beads, respectively.

5. The biological signal measuring device according to claim 1, wherein both spring constants of the first and second elastic members made of expanded resin beads obtained by load-deflection characteristics when the first and second elastic members made of expanded resin beads are disposed on the air cushion placed on a measuring stand, respectively, and the first and second elastic members made of expanded resin beads are pressed to a deflection amount of 1 mm by using a pressing plate with a diameter of 30 mm, respectively, are higher than a spring constant of the air cushion obtained from a load-deflection characteristic when only the air cushion is pressed to a deflection amount of 1 mm by using a pressing plate with a diameter of 30 mm, the spring constant of one of the first and second elastic members made of expanded resin beads falls within a range of 1.1 to 1.4 times the spring constant of the other, and a spring constant obtained from a load-deflection characteristic when the first and second elastic members made of expanded resin beads are stacked to each other to be disposed on the air cushion placed on a measuring stand and the first and second elastic members made of expanded resin beads are pressed to a deflection amount of 1 mm by using a pressing plate with a diameter of 30 mm falls within a range of 0.8 to 1.2 times the spring constant of only the air cushion.

6. The biological signal measuring device according to claim 1, wherein a three-dimensional solid knitted fabric is disposed within the airbag of the air cushion.

7. A biological state analyzing system comprising the biological signal measuring device according to claim 1; and
an electronic device configured to analyze a state of a person from an output signal of the sensor which detects air pressure fluctuation of the air cushion in the biological signal measuring device.

8. The biological state analyzing system according to claim 7, wherein the electronic device is configured to:
calculate a difference between an upper limit side peak value and a lower limit side peak value for each predetermined time range from peak values of each cycle of a time series waveform of an output signal obtained by the sensor in the biological signal measuring device, and utilize the difference as a power value to obtain time series data of the power value and perform slide calculation by a predetermined number of times to obtain a slope of the power value to a time axis in the predetermined time range;
obtain time series data of a maximum Liapunov index from the time series waveform of the output signal obtained by the sensor in the biological signal measuring device and perform slide calculation by a predetermined number of times to obtain a slope of the maximum Liapunov index to the time axis in the predetermined time range; and
when respective two slope time series waveforms obtained from the power value slope and the maximum Liapunov index slope are superimposed on each other, determine portions of the two slope time series waveforms which have opposite phases to each other as a sleep onset prediction signal.

9. The biological state analyzing system according to claim 8, wherein the electronic device is configured to differentiate the time series waveform of the output signal obtained from the sensor in the biological signal measuring device to obtain a differentiated waveform, and calculate a power value slope and a maximum Liapunov index slope from the differentiated waveform.

10. The biological state analyzing system according to claim 9, wherein the electronic device is configured to differentiate a time series waveform of the power value slope and a time series waveform of the maximum Liapunov index slope to obtain differentiated waveforms of the respective slope time series waveforms.

11. A biological signal measuring device comprising:
an air cushion provided with an airbag and a sensor which detects air pressure fluctuation of the airbag according to load fluctuation, wherein the air cushion is assembled between a skin member and a cushion supporting member arranged on a back face side of the skin member at a site supporting at least the vicinity of a lumbar area of a person, wherein
an elastic member made of expanded resin beads which has a size covering the air cushion is disposed between the skin member and the air cushion,
a three-dimensional solid knitted fabric is disposed within an airbag of the air cushion, and
the air cushion comprises a plurality of small airbags having a predetermined length and connected to one another in their length directions, where air is prevented from flowing between adjacent ones of the small airbags, and three-dimensional solid knitted fabrics disposed in the respective small airbags, and air pressure fluctuation of any of the small airbags is measured.

12. The biological signal measuring device according to claim 11, wherein the small airbag which measures the air pressure fluctuation is a small airbag of the plurality of small airbags which is positioned in an area where pulse waves of an aorta of a dorsal region of the person can be detected.

13. The biological signal measuring device according to claim 11, further comprising a seat provided with a seat cushion section and a seatback section, wherein the air cushion is disposed along a vertical direction of the seatback section, and the small airbag which measures the air pressure fluctuation has a width of 40 to 100 mm and a length of 120 to 200 mm and is provided such that an intersecting portion of one of side edges thereof positioned nearer to the center of the seatback section of the small airbag and a lower edge thereof is set to fall in a length range of 150 to 280 mm from an upper face of the seat cushion section along a surface of the seatback section and fall in a range of 60 to 120 mm from the center of the seatback section.

14. The biological signal measuring device according to claim 13, wherein the air cushion is configured such that two air cushions are provided at bilaterally symmetric positions regarding the center of the seatback section, and air pressure fluctuation of a small airbag in one of the two air cushions is measured.

15. The biological signal measuring device according to claim 14, wherein the respective air cushions have a width of 40 to 100 mm and an entire length of 400 to 600 mm, and
the respective air cushions are received in cushion receiving portions of a receiving body provided with a connection portion with a width of 60 to 120 mm and the cushion receiving portions provided on both sides of the connection portion, resulting in unitization.

16. The biological signal measuring device according to claim 14, wherein widths of the first and second elastic members made of expanded resin beads are equal to or longer than a length between top portions of the two air cushions.

17. A biological signal measuring device, comprising:
an air cushion provided with an airbag and a sensor which detects air pressure fluctuation of the airbag according to load fluctuation, wherein the air cushion is assembled between a skin member and a cushion supporting member arranged on a back face side of the skin member at a site supporting at least the vicinity of a lumbar area of a person, wherein
an elastic member made of expanded resin beads which has a size covering the air cushion is disposed between the skin member and the air cushion,
a three-dimensional solid knitted fabric is disposed within the airbag of the air cushion, and
the air cushion has a predetermined length and is configured such that at least two air cushions are stacked for use, a surface side air cushion of the at least two air cushions which is disposed on the side of the skin member comprises a plurality of small airbags connected to one another in their length directions, where air is prevented from flowing between adjacent ones of the small airbags, and three-dimensional solid knitted fabrics disposed in the respective small airbags, and air pressure fluctuation of any of the small airbags is measured.

\* \* \* \* \*